US010131900B2

(12) United States Patent
Pakhomova et al.

(10) Patent No.: US 10,131,900 B2
(45) Date of Patent: Nov. 20, 2018

(54) ELECTROPORATION-INDUCED ELECTROSENSITIZATION

(75) Inventors: Olga Pakhomova, Norfolk, VA (US); Andrei G. Pakhomov, Norfolk, VA (US)

(73) Assignee: OLD DOMINION UNIVERSITY RESEARCH FOUNDATION, Norfolk, VA (US)

( * ) Notice: Subject to any disclaimer, the term of this patent is extended or adjusted under 35 U.S.C. 154(b) by 521 days.

(21) Appl. No.: 13/994,508

(22) PCT Filed: Dec. 13, 2011

(86) PCT No.: PCT/US2011/064548
§ 371 (c)(1),
(2), (4) Date: Jun. 14, 2013

(87) PCT Pub. No.: WO2012/082688
PCT Pub. Date: Jun. 21, 2012

(65) Prior Publication Data
US 2013/0260435 A1     Oct. 3, 2013

Related U.S. Application Data

(60) Provisional application No. 61/423,203, filed on Dec. 15, 2010.

(51) Int. Cl.
*C12N 13/00* (2006.01)
*A61N 1/32* (2006.01)

(52) U.S. Cl.
CPC ............. *C12N 13/00* (2013.01); *A61N 1/327* (2013.01)

(58) Field of Classification Search
CPC ................................ C12N 13/00; A61N 1/327
See application file for complete search history.

(56) References Cited

U.S. PATENT DOCUMENTS

| | | | |
|---|---|---|---|
| 5,304,486 A * | 4/1994 | Chang | C12M 35/02 435/173.4 |
| 6,278,895 B1 | 8/2001 | Bernard | |
| 6,812,204 B1 | 11/2004 | McHale et al. | |
| 6,869,797 B2 | 3/2005 | Greener et al. | |
| 7,245,963 B2 | 7/2007 | Draghia-Akli et al. | |
| 7,332,332 B2 | 2/2008 | Riemen et al. | |
| 7,470,518 B2 | 12/2008 | Chiu et al. | |
| 7,668,592 B2 | 2/2010 | Heller et al. | |
| 7,758,561 B2 | 7/2010 | Eppstein | |
| 7,833,187 B2 | 11/2010 | Lepivert et al. | |
| 8,048,067 B2 | 11/2011 | Davalos et al. | |
| 2002/0025578 A1 | 2/2002 | MacLaughlin et al. | |
| 2002/0102729 A1 | 8/2002 | MacLaughlin et al. | |
| 2003/0198625 A1 | 10/2003 | Tseng et al. | |
| 2005/0171523 A1 | 8/2005 | Rubinsky et al. | |
| 2005/0171574 A1 | 8/2005 | Rubinsky et al. | |
| 2006/0024670 A1 * | 2/2006 | Luke | A61K 39/145 435/5 |
| 2006/0062074 A1 | 3/2006 | Gundersen et al. | |
| 2006/0264807 A1 | 11/2006 | Westersten et al. | |
| 2006/0269531 A1 * | 11/2006 | Beebe | A61N 1/0412 424/93.21 |
| 2007/0043345 A1 | 2/2007 | Davalos et al. | |
| 2007/0110736 A1 | 5/2007 | Riemen et al. | |
| 2008/0231337 A1 | 9/2008 | Krishnaswamy et al. | |
| 2008/0268542 A1 | 10/2008 | Rubio et al. | |
| 2008/0269586 A1 | 10/2008 | Rubinsky et al. | |
| 2009/0000948 A1 | 1/2009 | Wang et al. | |
| 2009/0053813 A1 | 2/2009 | Evans | |
| 2009/0197335 A1 | 8/2009 | Agrawal et al. | |
| 2009/0326436 A1 | 12/2009 | Rubinsky et al. | |
| 2010/0030211 A1 | 2/2010 | Davalos et al. | |
| 2010/0159439 A1 | 6/2010 | Orwar et al. | |
| 2010/0191157 A1 | 7/2010 | Sanghavi | |
| 2010/0227030 A1 | 9/2010 | Galindo et al. | |
| 2010/0261994 A1 | 10/2010 | Davalos | |

OTHER PUBLICATIONS

Potter "Transfection by Electroporation" (2003) in Current Protocols in Molecular Biology. 62:I:9.3:9.3.1-9.3.6.*
Al-Sakere et al., "Tumor ablation with irreversible electroporation", PLoS One (2007) 2(11): e1135. (8 pages).
Andre et al., "Efficiency of high- and low- voltage pulse combinations for gene electrotransfer in muscle, liver, tumor, and skin", Human gene Therapy (2008) 19: 1261-1271.
Ball et al., "Irreversible electroporation: A new challenge in "out of operating theater" anesthesia", Anasth Analg (2010) 110: 1305-1309.
Bilska et al., "Theoretical modeling of the effects of shock duration, frequency, and strength on the degree of electroporation", Bioelectrochemistry (2000) 51: 133-143.
El-Hag et al., "Inactivation of naturally grown microorganisms in orange juice using pulsed electric fields", IEEE Transactions on Plasma Science (2006) 34:1412-1415.
Escoffre et al., "What is (still not) known of the mechanism by which electroporation mediates gene transfer and expression in cells and tissues", Mol Biotechnol (2009) 41:286-295.
Esser et al., "Mechanisms for the intracellular manipulation of organelles by conventional electroporation", Biophysical Journal (2010) 98:2506-2514.
Faurie et al., "Electro-mediated gene transfer and expressionare controlled by the life-time of DNA/membrane complex formation", J Gene Med (2009) 12: 117-125.
Heller et al., "Electroporation gene therapy preclinical and clinical trials for melanoma", Curr Gene Ther (2010) 10:312-317.
Ibey et al., "Plasma membrane permeabilization by trains of ultrashort electric pulses", Bioelectrochemistry (2010) 79:114-121.

(Continued)

*Primary Examiner* — Teresa E Knight
(74) *Attorney, Agent, or Firm* — Nixon Peabody LLP; Eduardo J. Quinones

(57) ABSTRACT

Methods of enhancing membrane permeabilization in a cell are provided. A method includes disposing the cell between a first electrode and a second electrode and applying a plurality of electrical pulses between the first electrode and the second electrode. In the method, the plurality of electrical pulses include at least two trains of pulses separated by an interval greater than about 10 s. Further, the amplitude of the electrical pulses is selected to be greater than about 0.2 kV/cm.

21 Claims, 10 Drawing Sheets

(56) References Cited

OTHER PUBLICATIONS

Ibey et al., "Selective cytotoxicity of intense nanosecond-duration electric pulses in mammalian cells", Biochem Biophys Acta (2010) 1800:1210-1219.

Jayaram et al., "Optimization of electroporation waveforms for cell sterilization", IEEE T Ind Appl (2004) 40:1489-1497.

Jiang et al., "Frequency-dependent interaction of ultrashort E-fields with nociceptor membranes and proteins", Bioelectromagnetics (2010) 1-16.

Lebar et al., "Cell electropermeabilization to small molecules in vitro: Control by pule parameters", Radiol Oncol (2001) 35(3): 193-202.

Lebar et al., "Inter-pulse interval between rectangular voltage pulses affects electroporation threshold of artificial lipid bilayers", IEEE Transactions on Nonbioscience (2002) 1(3): 116-120.

Lebar et al., "Optimisation of pulse parameters In Vitro for In Vivo electrochemotherapy", Anticancer Research (2002) 22: 1731-1736.

Lebovka et al., "Food and biomaterials processing assisted by electroporation", Biological Effects of Electromagnetics CRC Press (2010) 1st ed.: 463-490.

Loghavi et al., "Effect of moderate electric field frequency and growth stage on the cell membrane permeability of Lactobacillus acidophilus", Biotechnol Prog (2009) 25(1): 85-94.

Maor et al., "Non thermal irreversible electroporation: Novel technology for vascular smooth muscle cells ablation", PLoS One (2009) 4(3): e4757. (9 pages).

Marty et al., "Electrochemotherapy—An easy, highly effective and safe treatment of cutaneous and subcutaneous metastases: Results of ESOPE (European Standard Operating Procedures of Electrochemotherapy) study", EJC Supplements (2006) 4: 3-13.

Miller et al., "Cancer cells ablation with irreversible electroporation", Technology in Cancer Research & Treatment (2005) 4(6): 699-705.

Mir et al., "Effective treatment of cutaneous and subcutaneous malignant tumours by electrochemotherapy", Br J Cancer (1998) 77:2336-2342.

Mir, "Nucleic acids electrotransfer-based gene therapy (electrogenetherapy): past, current, and future", Mol Biotechnol (2009) 43:167-176.

Nuccitelli et al., "A new pulsed electric field therapy for melanoma disrupts the tumor's blood supply and causes complete remission without recurrence", Int J Cancer (2009) 125:438-445.

Nuccitelli et al., "Optimized nanosecond pulsed electric field therapy can cause murine malignant melanomas to self-destruct with a single treatment", International Journal of Cancer (2010) 127: 1727-1736.

Pakhomov et al., "Lipid nanopores can form a stable, ion channel-like conduction pathway in cell membrane", Biochem Biophys Res Commun (2009) 385:181-186.

Palankar et al., "Pulsed electrical stimulation for control of vasculature: Temporary vasoconstriction and permanent thrombosis", Bioelectromagnetics (2008) 29: 100-107.

Pucihar et al., "The effect of pulse repetition frequency on the uptake into electropermeabilized cells in vitro with possible applications in electrochemotherapy", Bioelectrochemistry (2002) 57: 167-172.

Raeisi et al., "The effect of high-frequency electric pulses on tumor blood flow in vivo", J Membrane Biol (2010) 236: 163-166.

Rubinsky et al., "Optimal parameters for the destruction of prostate cancer using irreversible electroporation", J Urology (2008) 180: 2668-2674.

Sack et al., "Operation of an electroporation device for grape mash", IEEE Transactions on Plasma Science (2010) 38:1928-1934.

Schoenbach et al., "A scaling law for membrane permeabilization with nanopulses", IEEE Transactions on Dielectrics and Electrical Insulation (2009) 16:1224-1235.

Schoenbach et al., "Bioelectric effects of nanosecond pulses", IEEE Transactions on Dielectrics and Electrical Insulation (2007) 14:1088-1109.

Sersa et al., "Electrochemotherapy in treatment of tumours", Eur J Surg Oncol (2008) 34:232-240.

Sersa et al., "Electrochemotherapy of mouse sarcoma tumors using electric pulse trains with repetition frequencies of 1 Hz and 5 kHz", J Membrane Biol (2007) 236: 155-162.

Teissie et al., "Recent biotechnological developments of electropulsation. A prospective review", Bioelectrochemistry (2002) 55: 107-112.

Terpitz et al., "Electrofused giant protoplasts of *Saccharomyces cerevisiae* as a novel system for electrophysiological studies on membrane proteins", Biochim Biophys Acta (2008) 1778:1493-1500.

Tiwari et al., "Molecular and morphological characterization of somatic hybrids between Solanum tuberosum L. and S. etuberosum Lindt", Plant Cell Tiss Org (2010) 103:175-187.

Vernhes et al., "Chinese hamster ovary cells sensitivity to localized electrical stresses", Bioelectrochemistry and Bioenergetics (1999) 48: 17-25.

Vernhes et al., "Elimination of free-living amoebae in fresh water with pulsed electric fields", Water Research (2002) 36: 3429-3438.

Yang et al., "The effect of high frequency steep pulsed electric fields on in vitro and in vivo antitumor efficiency of ovarian cancer cell line skov3 and potential use in electrochemotherapy", Journal of Experimental & Clinical Cancer Research (2009) 28: 53-62.

Zupanic et al., "Increasing the repetition frequency of electric pulse delivery reduces unpleasant sensations that occur in electrochemotherapy", Neoplasma (2007) 54(3): 246-250.

International Search Report for PCT/US2011/064548; dated Feb. 24, 2012.

\* cited by examiner ical and theoretical studies using different endpoints reported significantly greater bioeffects at higher PRF [2, 3, 14, 31, 34-37], significantly greater effects at lower PRF [1, 5, 6, 11, 26, 30, 38-40], biphasic or more complex dependences [31, 40, 41], or relatively little role of PRF within studied limits [2, 9, 40, 42].

ELECTROPORATION-INDUCED ELECTROSENSITIZATION

CROSS-REFERENCE TO RELATED APPLICATIONS

This application is a § 371 national phase entry of International Application No. PCT/US2011/064548, filed Dec. 13, 2011, which claims priority to U.S. Provisional Patent Application No. 61/423,203, filed Dec. 15, 2010, the entire contents of both of which are incorporated herein by reference.

STATEMENT REGARDING FEDERALLY SPONSORED RESEARCH OR DEVELOPMENT

This invention was made with government support under R01CA125482 awarded by the National Institutes of Health/National Cancer Institute, and under R01GM088303 awarded by National Institutes of Health/National Institute of General Medical Sciences. The government has certain rights in the invention. With respect to any subject invention in which the Contractor retains title, the Federal government shall have a nonexclusive, nontransferable, irrevocable, paid up license to practice or have practiced for or on behalf of the United States the subject invention throughout the world.

FIELD OF THE INVENTION

The present invention relates to electroporation, and more specifically to methods for electroporation-induced electrosensitization.

BACKGROUND

Electroporation of cell membranes by electric pulses (EPs), also known as electropermeabilization, has been extensively studied for several decades. Experimental studies ranged from lipid bilayers and liposomes to both pro- and eukaryotic cells in culture and various tissues in vivo. Multiple theoretical studies explored the phenomenon of electropermeabilization by molecular dynamics, sophisticated electrical circuit modeling, and numerical simulations. Still, the mechanisms of electroporation itself and of electroporation-induced biological phenomena have not been fully understood, which stimulated a new surge of interest in the topic and numerous recent publications, e.g. [1-16].

In particular, electroporation has both well-established and developing applications for gene electrotransfer and gene therapy [15, 17-20] cell fusion [21-23], electro chemotherapy [24, 25], tumor ablation [4, 6, 14, 26], vascular smooth muscle cells ablation [5], sterilization [27, 28], and food processing [29, 30]. Numerous studies have focused on optimization of exposure conditions to produce maximum desired effect while minimizing side effects. However, with multiple parameters to consider (E-field, pulse duration, number of pulses, their shape, and repetition frequency) these studies have been laborious and showed limited success. The optimization process remains mostly empirical, whereas quantitative and mechanistic principles that determine the outcome of EP exposures are still being debated [8-11, 16, 31-33].

Out of different EP exposure parameters, the impact of the pulse repetition frequency (PRF) is the least understood, resulting in controversial findings and treatment recommendations. Aside from the trivial heating effect that increases with increased PRF (less time for heat dissipation), experimental and theoretical studies using different endpoints reported significantly greater bioeffects at higher PRF [2, 3, 14, 31, 34-37], significantly greater effects at lower PRF [1, 5, 6, 11, 26, 30, 38-40], biphasic or more complex dependences [31, 40, 41], or relatively little role of PRF within studied limits [2, 9, 40, 42].

Specifically, Vernier et al. [35] reported significant uptake of membrane impermeable dyes (propidium and YO-PRO-1) when Jurkat cells were exposed to 30 pulses (4-ns duration, 80 kV/cm) at 1 and 10 kHz rates. No dye influx was detected at the lower rates of 10 and 100 Hz. Jiang and Cooper [36] showed the reduction of the E-field threshold for nociceptor excitation from 30 to 24 and to 16 V/cm as the PRF was increased from 100 Hz to 1 and 4 kHz, respectively (for a train of one hundred 12-ns pulses). Similarly, applying 100-µs pulses at intervals under 1 ms lowered the electroporation threshold of artificial bilayer lipid membranes [34].

Increasing PRF from 0.1 to 1, 10, and 77 Hz (six 1-ms pulses at 800 V/cm) decreased the 24-hr survival of exposed CHO cells from 60% (0.1 Hz) to about 20% (77 Hz) [3]. Likewise, a train of 2,000 pulses (100-ns duration, 30 kV/cm) was more efficient in eliminating murine melanomas at PRF of 5 and 7 Hz when compared to 1 or 3 Hz [14]. However, the statistical significance of these findings was not evaluated. Overall, higher efficiency of higher PRF is usually attributed to the temporal summation of brief sub-threshold effects (or lesions) which can recover without consequences if the interval between pulses is sufficiently long.

In contrast to the above studies, Rubinsky and co-authors observed more efficient cell killing at lower PRF, both in vitro and in vivo [5, 6, 26, 39]. The authors typically adjusted several exposure parameters at once (in order to keep the cumulative EP duration or the total dose unchanged), so isolating "pure" effects of PRF may be not straightforward. Still, one can find that, for example, eight 1-ms pulses at 2.5 kV/cm were more efficient at 0.03 Hz than at 0.3 Hz; or eighty 100-µs pulses at 2.5 kV/cm were more efficient at 0.3 Hz than at 3 Hz (see FIG. 2 in [26]). When the delivered energy was kept constant, longer exposures at the lower E-field and using a greater number of pulses typically was more efficient, despite lower temperature rise. Gradual enhancement of the cytotoxic effect as the PRF decreased from 5 kHz to 1 kHz, 60 Hz, and 1 Hz was also reported in SKOV3 cells exposed to exponentially-decaying EPs [38]. The reason for higher efficiency of lower PRF has not been identified, but it may be related to the reduction of EP efficiency when the cell membrane is made "leaky" by the previous EPs [10, 41]. With longer inter-pulse intervals, the membrane partially reseals and the efficiency of the coming pulses increases. Simulation studies showed an overall slow decrease of the fractional area of pores with PRF increase, however, with sharp regular troughs at certain frequencies [41].

Pucihar and co-authors [40] found that the uptake of Lucifer Yellow dye by DC3F cells exposed to 26 pulses of 30-µs duration was the same for 1 Hz and 8.3 kHz, however, it required about 1.5 times higher E-field for the higher PRF. The dependence was similar for 100-µs pulses, except for a slightly higher dye uptake at 10 Hz compared to both lower (1 Hz) and higher PRF (1 and 2.5 kHz).

For a train of 200 pulses of 50-µs at 0.9 kV/cm, the cytotoxic effect in CHO cells showed a bell-shaped dependence on PRF: it was weaker at the central frequency of 10 Hz, and gradually enhanced as the rate either decreased to 0.5 Hz or increased to 100 Hz [31]. At the same time, propidium uptake by the cells was flat for the range from 0.5 to 20 Hz, and increased at 50 and 100 Hz. The authors hypothesized that the increased cytotoxicity at the lowest PRF may be related to slow rotation of cells in suspension, so that different portions of their membrane get exposed to the field and more membrane is porated. This idea was later extended into a complex model that related random statistical rotations of suspension cells to EP efficiency [11].

In the field of electrochemotherapy, a significant effort has been made in recent years to compare 1 Hz and 5 kHz delivery rates of 100-μs pulses. The advantage of the 5 kHz PRF was alleviation of pain and discomfort from EP application, whereas its anti-tumor efficiency was either similar, or somewhat higher, or somewhat lower, depending on the concurrent conditions and the method of assessment (for discussion, see [1, 42-44]).

SUMMARY

Embodiments of the invention concern methods of enhancing membrane permeabilization for a variety of applications. A method in accordance with the various embodiments can include disposing the cell (or multiple cells, tissue, tumor, etc) between at least a first electrode and a second electrode (or multiple electrodes) and applying a plurality of electrical pulses between the first electrode and the second electrode, wherein the plurality of electrical pulses comprise at least two train of pulses and separated by a duration of time greater than about 10 s, and wherein an amplitude of the electrical pulses is greater than about 0.2 kV/cm.

In the various embodiments, the total duration of time of the pulse trains can be from tens to hundreds of seconds.

The amplitude can be any value greater that 0.2 kV/cm, such as values between 0.2 kV/cm and 15 kV/com. For example, the amplitude can be greater than about 2 kV/cm, 3 kV/cm, 4.5 kV/cm, or 9 kV/cm.

The number of pulses can also vary in the various embodiments. For example the plurality of electrical pulses can be less than about 1500 pulses, 1000 pulses, or 500 pulses, such as about 100-150 pulses.

The interval between pulse trains can be 1, 5, 10, 15, or 30 minutes in some embodiments. Further, the first train and the second train can be substantially the same or different. For example, the number of electrical pulses in the first train can different than a number of electrical pulses in the second train such that the first train consists of 25% to 75% of the plurality of electrical pulses, such as 40% to 60% of the plurality of electrical pulses. In some configurations, the number of pulses can be substantially the same in both trains.

The various embodiments can be utilized to enhance permeability of or induce disintegration of various types of cells, including cancerous cells, mammalian cells, bacterial cells, and plant cells in a variety of applications.

In some embodiments, the method can further include introducing into at least one cell a therapeutic agent, wherein the therapeutic agent is selected from the group consisting of: nucleic acid, peptide, polypeptide, and drug.

In some embodiments, the disposing of the cell between the first electrode and the second electrode can consist of disposing a volume of liquid including the cell between the first electrode and the second electrode.

Unless otherwise defined, all technical terms used herein have the same meaning as commonly understood by one of ordinary skill in the art to which this invention belongs.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein, a "nucleic acid" or a "nucleic acid molecule" means a chain of two or more nucleotides such as RNA (ribonucleic acid) and DNA (deoxyribonucleic acid), and chemically-modified nucleotides. A "purified" nucleic acid molecule is one that is substantially separated from other nucleic acid sequences in a cell or organism in which the nucleic acid naturally occurs (e.g., 30, 40, 50, 60, 70, 80, 90, 95, 96, 97, 98, 99, 100% free of contaminants). The terms include, e.g., a recombinant nucleic acid molecule incorporated into a vector, a plasmid, a virus, or a genome of a prokaryote or eukaryote. Examples of purified nucleic acids include cDNAs, micro-RNAs, fragments of genomic nucleic acids, nucleic acids produced by polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

The phrases "isolated" or biologically pure" refer to material (e.g., nucleic acids) which is substantially or essentially free from components which normally accompany it as found in its native state.

The terms "patient," "subject" and "individual" are used interchangeably herein, and mean an animal (e.g., a mammal such as a human, a vertebrate) subject to be treated and/or to obtain a biological sample from.

As used herein, the terms "therapeutic," and "therapeutic agent" are used interchangeably, and are meant to encompass any molecule, chemical entity, composition, drug, therapeutic agent, chemotherapeutic agent, or biological agent capable of preventing, ameliorating, or treating a disease or other medical condition. The term includes small molecule compounds, drugs, antisense reagents, siRNA reagents, antibodies, enzymes, peptides organic or inorganic molecules, cells, natural or synthetic compounds and the like.

As used herein, the term "treatment" is defined as the application or administration of a therapeutic agent to a patient or subject, or application or administration of the therapeutic agent to an isolated tissue or cell line from a patient or subject, who has a disease, a symptom of disease or a predisposition toward a disease, with the purpose to cure, heal, alleviate, relieve, alter, remedy, ameliorate, improve, prevent or affect the disease, the symptoms of disease, or the predisposition toward disease.

By the phrases "therapeutically effective amount" and "effective dosage" is meant an amount sufficient to produce a therapeutically (e.g., clinically) desirable result; the exact nature of the result will vary depending on the nature of the disorder being treated. The compositions and cells described herein can be administered from one or more times per day to one or more times per week. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions and cells described herein can include a single treatment or a series of treatments.

DETAILED DESCRIPTION

Figure 1A:
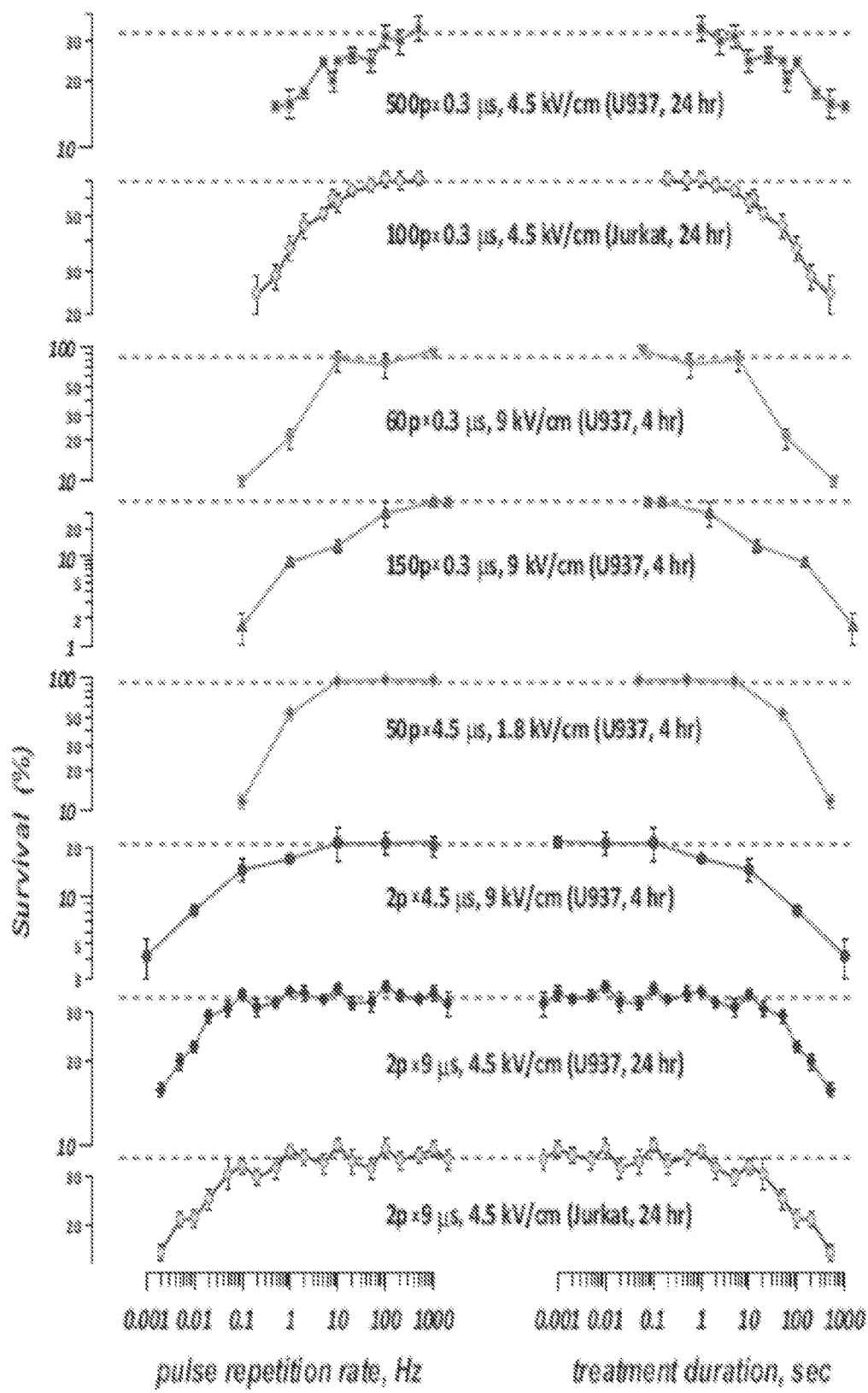
FIG. 1A is a series of log-log plots showing the effect of the pulse repetition rate (plots on left side) and of the total duration of the treatment (plots on right side) on cell survival.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As noted above, EP-based treatments have been studied extensively. However, none of the above-mentioned studies was specifically focused on the role of PRF. Instead, PRF was just one of several variables evaluated alongside other parameters of interest. This lack of comprehensive, wide scale studies may explain, at least partially, the controversy concerning PRF impact and mechanisms involved.

The present inventors have discovered that the efficiency of varied EP treatments was increased when the treatment duration was made sufficiently long, either by applying pulses at a low rate, or by splitting a single pulse train into separate fractions. This increase in efficiency is explained by a gradual and delayed increase in the EP susceptibility during the exposure procedure. In other words, the EP (or EPs) that are delivered first cause sensitization to subsequently delivered EPs, thereby increasing their effect and making the entire EP treatment more efficient. It is well established that the principal and primary effect of intense electric pulses in living cells is electroporation of the cell plasma membrane, which allows the observed increase in EP efficiency to be interpreted as the electroporation-induced electrosensitization.

The studies discussed above attempted to explain various pulse rate effects relying solely on the physical effects of the applied electric field. However, none of these explanations can explain the delayed sensitization (which requires at least 10-100 sec of the total treatment duration) or predict the effect of the fractionated treatments. The data point to a biological rather than merely physical mechanism of sensitization. The present inventors describe below some types of cellular events could lead to sensitization.

For example, once the cell is electroporated by the first pulse(s) of the EP exposure, the ions from the extracellular medium diffuse into the cell, down the concentration and electrochemical gradients, whereas the intracellular ions leave the cell. The cell attempts to restore the ion gradients and membrane potential by activating ion pumps and repairing the membrane [48, 49]. High energy expenditure for these processes may be aggravated by ATP leakage out of cells through the electropores. One can speculate that a prolonged high demand for ATP combined with ATP loss during longer exposures could be a factor responsible for sensitization.

Among ions that can enter through the electropores, $Ca^{2+}$ will have multiple effects on cell physiology. It is not clear how exactly the increased $Ca^{2+}$ concentration would change the cell susceptibility to EP, but it should come as no surprise that prolonged time intervals when the internal $Ca^{2+}$ is elevated (e.g., due to a longer EP treatment) may be unfavorable for cells and make them more vulnerable.

Plasma membrane permeabilization also triggers cell volume changes due to the so-called colloid osmotic mechanism [47, 50]. In a "typical" bath buffer, as well as in the cell growth medium, permeabilization leads to water uptake and cell swelling. The increase of cell diameter translates into a higher induced membrane potential when next EPs are applied [23], which makes electroporation more efficient. Furthermore, the additional membrane for cell swelling is recruited from cytoplasmic invaginations of the plasma membrane, and this "spreading out" of the membrane could also contribute to increasing EP effects.

Notably, considering these mechanisms helps to reconcile the seemingly contradictory studies that reported diverse effects of PRF. For example, Faurie and co-authors [3] reported greater cytotoxic effect of 1-ms pulses as the PRF was increased from 0.1 to 77 Hz, which is the opposite of what was shown in our work and other studies [5, 6, 26, 39].

The present inventors have determined that one aspect of understanding the underlying mechanisms of the invention is the composition of the pulsing medium. For example, as described in further detail below, the one exemplary pulsing medium contains 250 mM sucrose, 1 mM $MgCl_2$, and 10 mM of $K_2HPO_4/KH_2PO_4$ buffer [3]. In this medium, membrane electroporation obviously will not lead to any $Ca^{2+}$ or $Na^+$ uptake, and cell swelling will be weaker or even replaced by shrinking. Thus, the lack of electroporation-induced electrosensitization in this and similar pulsing mediums is consistent with the involvement of one or several mechanisms mentioned above.

Another potential mechanism of electrosensitization may involve direct or indirect oxidative damage to membrane by EP exposure [51-53], which would enhance its susceptibility to permeabilization by EPs [54].

Although the exact sequence of events resulting in electrosensitization has yet to be identified, taking this phenomenon into account helps to explain contradictions in published data, and will likely be beneficial for many existing and coming applications of electroporation. Controlled cell destruction with minimum side effects and energy expenditure is the principal endpoint in tissue and tumor ablation, sterilization, and food processing, whereas in other applications such as gene electrotransfer, the cell death is a major outcome to avoid. Engaging (or preventing) electrosensitization by changing pulse rate and by exposure fractionation can be a simple and efficient approach to achieve the desired goals of various electroporation treatments.

The present inventors have found that intense, brief electric pulses triggered gradual and delayed development of electrosensitization, which profoundly increases the sensitivity of treated cells to subsequent EP exposure. The present inventors have determined that the sensitized state can be generated by increasing treatment times. In particular, by providing a fractionated exposure, i.e., splitting a single EP train into separate trains with a sufficiently long interval between them (>10 s) and applying the EPs over a long enough period of time (10 s to 100 s of seconds), electrosensitization develops. In these types of exposure, a first portion of the EPs sensitize cells to EPs that arrive later, thereby markedly increasing the cytotoxic efficiency of EP exposure as a whole. Such electrosensitization makes it possible to lower the exposure intensity (use lower E-field, fewer number of pulses, shorter pulse duration) while achieving the same biological effect; similarly, a greater bioeffect can be produced just by modifying the protocol of EP delivery, without increasing the exposure intensity.

Traditionally, the sensitivity of biological cells to electroporation has been viewed as an electrochemical phenomenon, but a number of investigators acknowledged that they were unable to explain the experimental data solely by physical models. The phenomenon of electrosensitization now adds a biological dimension to understanding the cell susceptibility to EP treatments and enables reconciliation of controversial experimental findings.

Thus, changing the pulse delivery protocol in accordance with the various embodiments so as to induce electrosensitization (or, for other applications, to avoid it) is a simple yet promising technique to maximize the desired effects of EP treatment while reducing harmful side effects.

In view of the foregoing, the various embodiments of the invention therefore provide new methods for treating cells using particular configurations of pulse trains. In the systems and methods in accordance with the various embodiments, the cells can be disposed between electrodes. The electrodes can be coupled to a power supply and associated control system for providing a plurality of pulses to the electrodes in order to generate an electric field for treating the cells.

The treatment in the various embodiments consists of applying a plurality of pulses across the electrode for a period of at least 10 seconds. The duration results in earlier pulses electrosensitizing the cells prior to the later pulses. However, the various embodiments are not limited in this regard and treatment durations can exceed 10 to 1000 seconds. Further, the pulses can be configured to have an amplitude of at least 0.2 kV/cm. However, the amplitude can be any value greater that 0.2 kV/cm, such as values between 0.2 kV/cm and 15 kV/cm, including, but not limited to about 2 kV/cm, 3 kV/cm, 4.5 kV/cm, or 9 kV/cm. At higher pulse amplitudes, electrosensitization can be induced with a lower number of pulses. Accordingly, as the amplitude is increased from 2 kV/cm to 9 kV/cm, the number of pulses can be decreased from about 2000-1500 pulses to about 100-150 pulses while still observing electrosensitization.

In particular, the various embodiments utilize a fractionated exposure to increase the total treatment duration without increasing exposure (i.e., without requiring additional pulses). That is, the electrodes are configured for sequentially applying at least a first and a second train of electrical pulses between the first electrode and the second electrode and with an interval between them. For example, the pulse trains can be configured to occur at least around 10 seconds apart. However longer intervals of time can be used to separate the pulse trains. For example, the pulse trains can be 1, 5, 10, 15, or even 30 minutes apart depending on the types of cells being treated and the configuration of the pulses.

In the various embodiments, the pulse trains for the fractionated approach can be configured in a variety of ways. For example, in some embodiments, the first train and the second train are substantially the same. However, the various embodiments are not limited in this regard and the pulse trains can also be substantially different. That is, the pulse trains can be the same or vary with respect to electric field, the total number of pulses, the pulse repetition rate, and the length and shape of the pulses, to name a few. The various embodiments are not limited solely to these parameters and any other parameters for control or generating the pulse trains can be the same or different for the first and second trains.

The various parameters described above can vary over wide ranges in the various embodiments. However, for at least some of these parameters, values can be selected to further enhance electrosensitization. For example, although the electric field can be in a range from about 0.2 kV/cm to about 15 kV/cm in the various embodiments, the electric field values can be adjusted to enhance sensitization, as described above.

In another example, the fraction of pulses in the first and second trains can be selected to enhance sensitization. In particular, the fraction of pulses in each of the trains can be selected to be substantially equal. For example, by including at least 25% to 75% of the pulses to be applied in the first train. Further, a more even split of pulses can be provided in the first train, such as between 40% and 60%, including 50%.

Further, a combination of approaches can be used. For example, treatment effectiveness can be improved by using pulse trains with and combination of higher electric fields, lower repetition rates, and substantially equal fractions of pulses.

The methodology described above can be used for a variety of applications. Some exemplary applications are listed below. However, these are provided for exemplary purposes only and the various embodiments are not limited in this regard.

The methods described herein may be used to enhance membrane permeabilization of cells in in vitro, in vivo and ex vivo settings. In some applications, the cells can be cancerous cells. Accordingly, exposure to such electric fields can be used to induce cell death in order to destroy or shrink tumors (e.g., in vivo treatment of cancerous tumors in a subject such as a human). The methods described herein can be used for the treatment of any aberrant or neoplastic cell growth. Examples of neoplasia disorders include acral lentiginous melanoma, actinic keratoses, adenocarcinoma, adenoid cystic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epithelioid, Ewing's sarcoma, fibrolamellar, focal nodular hyperplasia, gastrinoma, germ cell tumors, glioblastoma, glucagonoma, hemangioblastomas, hemangioendothelioma, hemangiomas, hepatic adenoma, hepatic adenomatosis, hepatocellular carcinoma, insulinoma, intraepithelial neoplasia, interepithelial squamous cell neoplasia, invasive squamous cell carcinoma, large cell carcinoma, leiomyosarcoma, lentigo maligna melanomas, leukoplakias, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

In some embodiments, a treatment involving enhancing membrane permeabilization as described herein may precede, or follow, a second anti-cancer treatment by, e.g., intervals ranging from minutes to weeks. The therapeutic methods involving enhancing membrane permeabilization as described herein may be combined with any other methods generally employed in the treatment of the particular tumor, disease or disorder that the patient exhibits. It also is envisioned that more than one administration of either the composition or another anti-cancer agent will be utilized. A treatment involving enhancing membrane permeabilization as described herein and a treatment with an anti-cancer agent (e.g., anti-cancer drug) may be administered interchangeably, on alternate days or weeks; or a sequence of the treatment involving enhancing membrane permeabilization followed by a sequence of anti-cancer agent therapy. In any event, to achieve tumor regression using a combined therapy, all that is required is to deliver both treatments in an effective amount to exert an anti-tumor effect, irrespective of the times for administration. A combination therapy for treating cancer may include, for example, surgical resection of a tumor. In terms of surgery, any surgical intervention may be practiced in combination with the treatments involving enhancing membrane permeabilization as described herein.

In addition to ablation of cancerous tissue, the methods described herein can be used to ablate any unwanted tissue. For example, warts, condilomas, unwanted heart tissue that causes arrhythmia can be ablated using these methods (similar to radiofrequency ablation). In another embodiment, the methods described herein can be used to sterilize surfaces and devices. For example, the methods can be used for the removal of bacterial biofilms from a surface (e.g., from medical devices). The methods can be used on any area where electroporation is used—causing the electroporation to be more efficient, and/or allowing the electroporation to reach the same efficiency at a lower energy expenditure, lower heating, with reduced side effects, etc.

In other applications, the methods described above can be used to provide permeabilization in order to enhance the delivery of a therapeutic agent in in vitro, in vivo and ex vivo settings. A therapeutic agent that can be used in the various embodiments can include, but is not limited to: nucleic acid, peptide, polypeptide, and drug. Conditions for introducing therapeutic agents into subjects by membrane permeabilization in vivo are known in the art (e.g., see T. Murakami and Y. Sunada, Curr Gene Ther. October 21; 11(6)). Therapeutic agents can be introduced into any suitable tissue type in vivo. Skeletal muscle, for example, is a well characterized target tissue for electroporation, because it is accessible and allows for long-lasting gene expression (>one year). As another example, skin is also a target tissue because of its accessibility and immunogenicity. Ex vivo delivery of cells into which a therapeutic agent (e.g., nucleic acids such as vectors, plasmids, etc.) has been introduced by enhancing membrane permeabilization is encompassed by the methods described herein. Ex vivo gene delivery is used to transplant, for example, host cells into which a therapeutic agent (e.g., nucleic acids such as vectors, plasmids, etc.) has been introduced back into the host (e.g., patient, subject in need thereof). A suitable ex vivo protocol may include several steps. For example, a segment of target tissue or cells may be harvested from the host and a method of enhancing membrane permeabilization in at least one cell may be used to introduce into the host cells a therapeutic agent such as a nucleic acid. These genetically modified cells may then be transplanted back into the host (e.g., patient, subject in need thereof).

In some cases, the therapeutic agent can be used in combination with configurations for inducing cell death. This configuration allows exposure to electric fields to be further limited.

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Conventional methods of culturing mammalian cells, e.g., human podocytes, are generally known in the art. Conventional methods of gene transfer and gene therapy may also be adapted for use in the present invention. See, e.g., Gene Therapy: Principles and Applications, ed. T. Blackenstein, Springer Verlag, 1999; and Gene Therapy Protocols (Methods in Molecular Medicine), ed. P. D. Robbins, Humana Press, 1997.

The compositions and cells described herein may be administered to mammals (e.g., rodents, humans) in any suitable formulation. A description of exemplary pharmaceutically acceptable carriers and diluents, as well as pharmaceutical formulations, can be found in Remington's Pharmaceutical Sciences, a standard text in this field, and in USP/NF. The compositions and cells described herein are preferably administered to a mammal (e.g., human) in an effective amount, that is, an amount capable of producing a desirable result in a treated mammal (e.g., treating cancer). Such a therapeutically effective amount can be determined according to standard methods. Toxicity and therapeutic efficacy of the compositions utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently.

The various embodiments can also be useful for the processing of foods. In one example, the various embodiments can be used to pre-treat fruits, vegetables, and other plant products to induce electroporation and facilitating extraction of liquids therefrom. That is, by inducing electroporation, extraction of liquids from the cells of plant products is facilitated. In another example, the electroporation can be used to enhance drying, freeze-drying, freezing, and rehydration behavior of such plant products. In still another example, the various embodiments can be used for inactivating bacterial cells in liquid foodstuffs. That is, the various embodiments can be used for the disintegration of bacterial cells in a liquid.

Examples

The following non-limiting Examples serve to illustrate selected embodiments of the invention. It will be appreciated that variations in proportions and alternatives in elements of the components shown will be apparent to those skilled in the art and are within the scope of embodiments of the invention.

Cell Lines and Propagation

Experiments were performed in two suspension cell lines (Jurkat clone E6-1, human T-lymphocytes, and U-937, human monocytes) and one anchor-dependent cell line (CHO-K1, Chinese hamster ovary). The cells were obtained from ATCC (Manassas, Va.) and propagated at 37° C. with 5% $CO_2$ in air according to supplier's recommendations. Jurkat and U-937 cells were grown in RPMI-1640 medium supplemented with 10% fetal bovine serum and 2 mM L-glutamine. CHO cells were propagated in Ham's F12K medium supplemented with 10% FBS. The media also contained 1% penicillin/streptomycin. The media and its components were purchased from Mediatech Cellgro (Herdon, Va.) except for serum (Atlanta Biologicals, Norcross, Ga.).

EP Exposure and Viability Assays for Suspension Cell Lines

Cells were harvested during the logarithmic growth phase, pelleted by centrifugation, and resuspended in fresh growth medium at either 0.6 or $1.2 \times 10^6$ cells/ml. The suspension was dispensed into conventional electroporation cuvettes with 1- or 2-mm gap between the electrodes (Bio-Smith Biotech, San Diego, Calif.). The cuvettes were exposed to EPs at room temperature (21-23° C.), one cuvette at a time. The exposure protocols were organized so that to (1) minimize waiting of aliquoted cells for EP exposure to less than 10 min (on a few occasions, up to 20 min), (2) ensure the same treatment conditions for parallel samples, so that the only variable would be the EP exposure regimen, and (3) carefully randomize all EP treatments, including "sham" exposures.

Unipolar EPs of 300-ns, 4.5- or 9.0-µs duration and up to 1-kV amplitude were generated by an AVTECH AVOZ-D2-B-ODA pulser (AVTECH Electrosystems, Ottawa, Ontario, Canada). To produce pulse trains of predetermined duration at selected pulse repetition rates, this generator was triggered externally from a model 58800 stimulator (Grass Instruments Co., Quincy, Mass.). The pulse amplitude and shape (trapezoidal, with rise and fall times (20%-80%) of <100 ns) were monitored using a Tektronix TDS 3052B oscilloscope. Pulses were delivered to the electroporation cuvette using a 50- to 10-Ohm transition module (AVOZ-D2-T, AVTECH Electrosystems) modified into a cuvette holder. The E-field values were obtained by dividing the mean pulse voltage (as measured by the oscilloscope) by the width of the gap in the electroporation cuvette. The absorbed dose was calculated as the energy delivered to the sample normalized to the mass of the sample [51].

Sample temperature during and after EP exposure was checked with a fiber optic ReFlex-4 thermometer (Nortech Fibronic, Quebec City, Quebec, Canada), and never exceeded 30° C.

Cell survival was measured either in 24 hr post exposure using MTT (3-(4,5-Dimethylthiazol-2-yl)-2,5-diphenyltetrazolium bromide) assay, or in 4 hr post exposure by a fluorescent dye exclusion/quenching method.

For the MTT assay (BioAssay Systems, Hayward, Calif.), exposed cells were aseptically aliquoted into a 96-well plate, in triplicates at $50 \times 10^3$ cells/well, and diluted to 100 µl with fresh growth medium. The plate was incubated at 37° C., with 5% $CO_2$ in air. At 20 hr after EP treatment, 10 µl of the MTT reagent were added to each well, and incubation continued for additional 4 hr. Formed blue formazan crystals were dissolved by adding the solubilization buffer (100 µl/well) and placing the plate on an orbital shaker overnight. Absorbance at 570 nm was read the next day using Synergy 2 microplate reader (BioTEK, Winooski, Vt.).

With the MTT assay, cell survival was considered proportional to the sample absorbance, and was expressed in % to the absorbance of the sham-exposed parallel control samples. The results are presented in the graphs and text as mean values+/−s.e. for a minimum of three independent experiments (usually 5-12 experiments).

For the dye exclusion/quenching method, aliquots of exposed cells were transferred into microcentrifuge tubes and left in the incubator until analysis (the tube lid was left open). At 4 hr post exposure, 20 µl of the cell suspension were mixed with equal volume of staining solution (100 µg/ml of propidium iodide and 0.5 µg/ml of acridine orange in phosphate-buffered saline). The dyes and chemicals were purchased from Sigma-Aldrich (St. Louis, Mo.). The sample was immediately loaded into a counting chamber of the automated cell counter Cellometer Vision with two-channel cell fluorescence detection (Nexcelom Bioscience LLC, Lawrence, Mass.).

Both employed dyes markedly increase fluorescence upon binding to DNA; while acridine orange readily penetrates the intact cell membrane, propidium does not. Live cells were distinguished by bright fluorescence of acridine orange (excitation/emission 475/535 nm). In cells with damaged membrane (presumably dead), this signal was quenched by fluorescence resonance energy transfer to propidium that entered the cell and bound to DNA. Combined fluorescence of either acridine orange or propidium (excitation/emission 525/595 nm) was used to determine the total (live+dead) cell count.

When using the dye exclusion/quenching assay, cell survival was expressed as a percentage of live cells to the total number of cells counted in each slide (usually several hundreds of cells), and two slides were processed for each datapoint. The survival data were presented as a mean+/−s.e for 3-7 independent experiments.

EP Exposure of Individual Cells on a Coverslip and Fluorescent Microscopy

The procedures were similar to those described recently [12, 55]. For the passage immediately preceding experiments, CHO cells were transferred onto glass cover slips pre-treated with poly-L-lysine to improve cell adhesion. After several hours, a cover slip with cells was transferred into a glass-bottomed chamber (Warner Instruments, Hamden, Conn.) mounted on an Olympus IX71 inverted microscope equipped with an FV 300 confocal laser scanning system (Olympus America, Center Valley, Pa.). The chamber was filled with a buffer composed of (in mM): 136 NaCl, 5 KCl, 2 $MgCl_2$, 2 $CaCl_2$, 10 HEPES, and 10 Glucose (pH 7.4), with addition of 30 µg/ml of propidium iodide. The buffer osmolality was at 290-300 mOsm/kg, as measured with a freezing point microosmometer (Advanced Instruments, Inc., Norwood, Mass.). The chemicals were purchased from Sigma-Aldrich.

EPs were delivered to a selected cell (or a group of 2-4 cells) with a pair of tungsten rod electrodes (0.08-mm diameter, 0.15 mm gap). With a help of a robotic micromanipulator (MP-225, Sutter, Novato, Calif.), these electrodes were positioned precisely at 50 µm above the coverslip surface so that the selected cells were in the middle of the gap between their tips. Nearly rectangular 60-ns pulses were generated in a transmission line-type circuit, by closing a MOSFET switch upon a timed delivery of a TTL trigger pulse from pClamp software via a Digidata 1322A output (MDS, Foster City, Calif.). The exact PRF, the EP delivery protocol, and synchronization of EP delivery with image acquisitions were programmed in pClamp.

The E-field between the electrodes was determined by 3D simulations with a finite element Maxwell equations solver Amaze 3D (Field Precision, Albuquerque, N. Mex.). The exact EP shapes and amplitudes were captured and measured with a Tektronix TDS 3052 oscilloscope.

Differential-interference contrast and fluorescent images of cells (excitation: 488 nm; emission 605 nm) were collected every 10 sec (starting exactly 50 s prior to the first EP) using a 60×, 1.42 NA oil objective. Photomultiplier tube settings were biased towards high sensitivity and detection of even minimal propidium uptake, although massive uptake caused detector saturation. Images were quantified with MetaMorph v. 7.5 (MDS). All experiments were performed at a room temperature of 22-24° C.

Effect of PRF on Long-Term Cell Survival

Figure 1B:
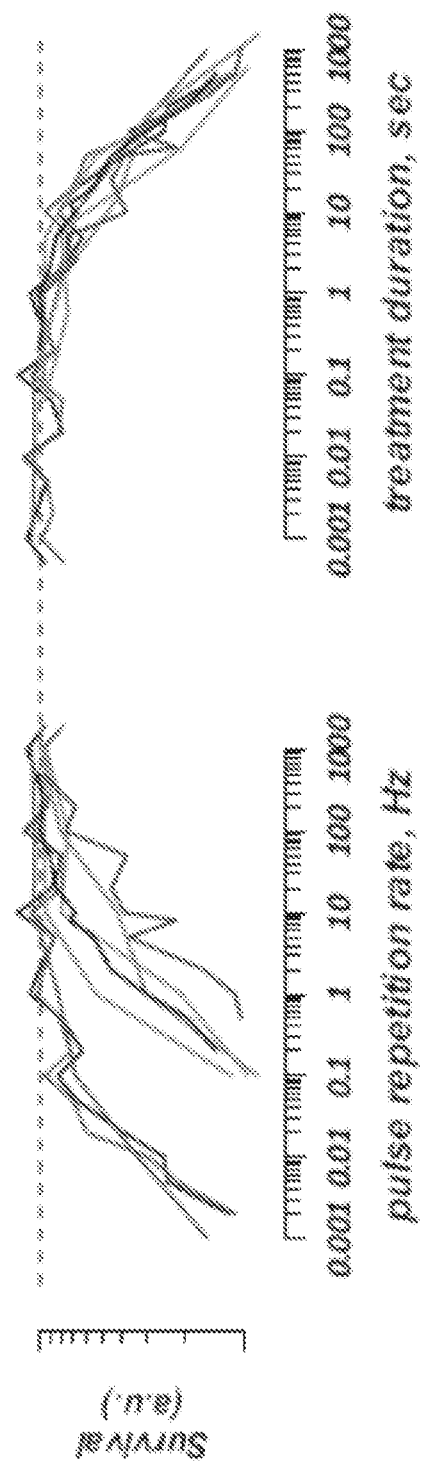
FIG. 1B shows log-log plot combining the results of FIG. 1A, thus summarizing the effect of the pulse repetition rate (plot on left side) and of the total duration of the treatment (plot on right side) on cell survival for the various conditions in FIG. 1A.

Turning first to FIG. 1A, FIG. 1A is a series of log-log plots showing the effect of the pulse repetition rate (plots on left side) and of the total duration of the treatment (plots on right side) on cell survival. Each plot in FIG. 1A represents a separate series of experiments where cells were exposed to a fixed number of pulses of a given amplitude and duration (see legends within the figure; e.g., for the top plot the legend means "500 pulses of 0.3 µs duration at 4.5 kV/cm). The only variable in each series was the pulse repetition rate and, consequentially, the total duration of the treatment. Other data in the legends are the cell type (U937 or Jurkat) and the timepoint after exposure when the cell survival was measured (4 hr or 24 hr). Each datapoint is the mean+/−s.e for 3-12 independent experiments. FIG. 1B shows log-log plot combining the results of FIG. 1A, thus summarizing the effect of the pulse repetition rate (plot on left side) and of the total duration of the treatment (plot on right side) on cell survival for the various conditions in FIG. 1A.

The plots on the left hand side of FIG. 1A show the results of multiple experiments that tested the cytotoxic efficiency of EP trains delivered at different PRF. Each plot corresponds to an independent set of experiments where the E-field, pulse duration, and the number of pulses were kept constant, while the PRF was the only parameter varied. Overall, these experiments explored rather diverse exposure conditions: 300 ns to 9 µs pulse duration, 1.8 to 9 kV/cm E-field, 2 to 500 pulses per train, at 0.001 to 1,000 Hz P R F. In addition, the experiments were performed in two cell lines (Jurkat and U937), and cell survival was measured by different methods.

Regardless of the specific conditions tested, maximum cell killing in all experiments was achieved at the lowest tested PRF. As the PRF increased, the effect gradually weakened and reached a plateau at higher frequencies. The level at which the plateau was reached differed more than 1000-fold from one set of experiments to another, as shown by the variation in occurrence of plateaus in FIG. 1A. FIG. 1B shows that the increase of the EP efficiency from the minimum plateau level occurred at PRFs as different as 0.1-500 Hz. Such diversity was difficult to explain and suggests that perhaps it was not the PRF alone that actually determined the increased effect at the lower pulse rates.

To check this idea, the same data were re-plotted against the total duration of the treatment, which was simply a ratio of the pulse number to the PRF. These are shown in the plots of FIG. 1A on the right. The data from the different sets of experiments now showed much better agreement: in all cases, the transition from the plateau to higher cytotoxic efficiency corresponded to the treatment duration of about 10 sec (FIG. 1, bottom graph in the right column). For the bottom plots, the curves from all series of experiments were collapsed together; shown are only the connecting lines; the mean value symbols and error bars have been omitted for clarity. See text for more detail.

Interpretation of this finding is easier when considering the exposures that consisted of only two pulses (bottom three sets of plots in FIG. 1A). In this case, the treatment duration was simply the interval between the pulses, and the cytotoxic efficiency increased once a certain interval was exceeded. These data prompt that the first pulse conditioned the cells, making them more sensitive to the second pulse if it is delivered after a proper delay. The validity of this explanation also for multi-pulse treatments is confirmed below by exposure fractionation.

Therefore, FIGS. 1A and 1B shows that the EP cytotoxic effect is enhanced when the total duration of the treatment exceeds a certain minimum. To test if this enhancement was indeed unrelated to a change in PRF, the present inventors increased the treatment duration while keeping both the PRF and the number of pulses constant. Specifically, by splitting of a high rate EP train into separate fractions separated by a long quiescent period or interval. The effect of such exposure fractionation is illustrated in FIG. 2.

Figure 2:
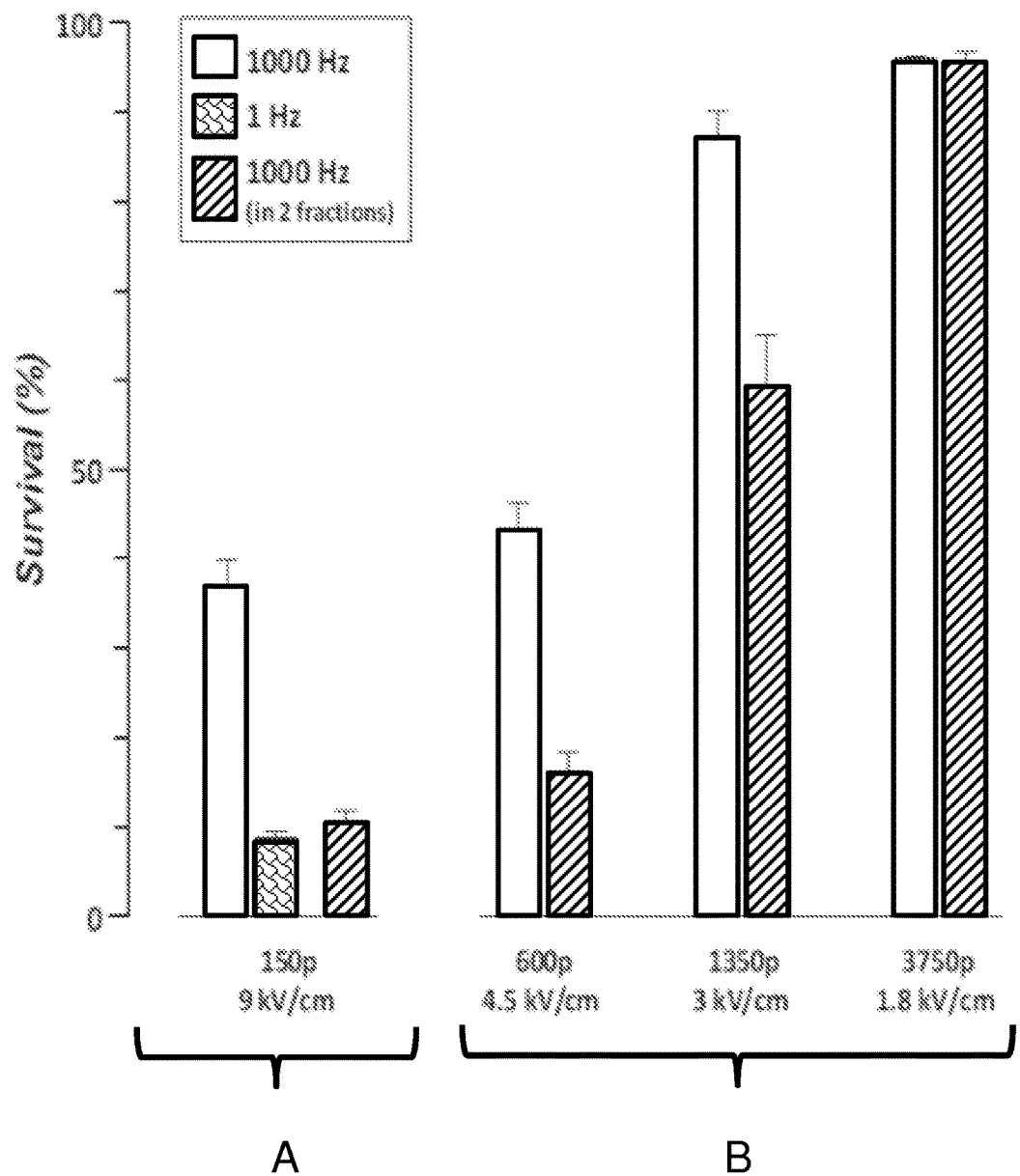
FIG. 2 is a bar chart showing survival for different exposure conditions.

FIG. 2 is a bar chart showing survival for different exposure conditions. For group A in FIG. 2, a train of 150 pulses (300 ns, 9 kV/cm) was evaluated for pulse repetition rates of 1 Hz and 1000 Hz. Additionally, a fractionated pulse was provided under the same conditions with a pulse repetition rate of 1000 Hz. As shown by the data in group A, the train of pulses was far more efficient at 1 Hz than at 1,000 Hz. The respective train durations and cell survival levels were 150 s and 8.4+/−1.1% versus 0.15 s and 37+/−2.8% (p<0.01, Student's t-test). However, when the 1,000 Hz train was split into two fractions (75 pulses, 0.75 s each) separated by a 150-s interval, the resulting cell survival dropped to 10.6+/−1.1%, i.e., it became the same as after the 1 Hz, 150-s exposure.

This demonstrates that it was indeed the treatment duration, rather than a particular PRF, that determined the enhancement of the cytotoxic effect. When the duration of the 1,000 Hz EP treatment was increased by splitting one train in two fractions to match the duration of the 1 Hz treatment, both the 1000 Hz and 1 Hz exposures had the same effect.

Turning now to group B in FIG. 2, group B shows enhancement of the EP cytotoxic effect by exposure fractionation. For FIG. 2, U937 cells were exposed 0.3 µs EPs; the pulse number, amplitude, and delivery mode (fractionated or not), are indicated in the figure. Cell survival was measured as a percentage of propidium-excluding cells at 4 hr post exposure (mean+/−s.e., n=3-7). Survival in sham-exposed samples was over 95% (data not shown). As previously discussed with respect to group A, exposure to 150 pulses was significantly more effective at 1 Hz than at 1,000 Hz and splitting the 1,000 Hz train in two fractions of 75 pulses each, with a 150 s interval, made it as efficient as the 1 Hz treatment. Group B shows similar results. That is, the splitting of a single high-rate train in two same size fractions with 150-s interval enhanced the effect EP of 4.5 and 3 kV/cm EPs, but not at the lower EP amplitude of 1.8 kV/cm.

The data for group B shows that fractionation enhanced the effect for different exposure conditions, but excluding those when the E-field was reduced to a sub-threshold value (1.8 kV/cm). When a single train had no appreciable effect on cell survival, splitting it in fractions had no additional effect.

However, the lack of appreciable cytotoxic effect of a high-PRF exposure does not necessarily always indicate the lack of subthreshold lesions. Under certain conditions, such subthreshold lesions can be amplified by slower or fractionated treatments to cause a profound drop in survival (e.g., see FIG. 1A, fifth set of plots).

Figure 3:
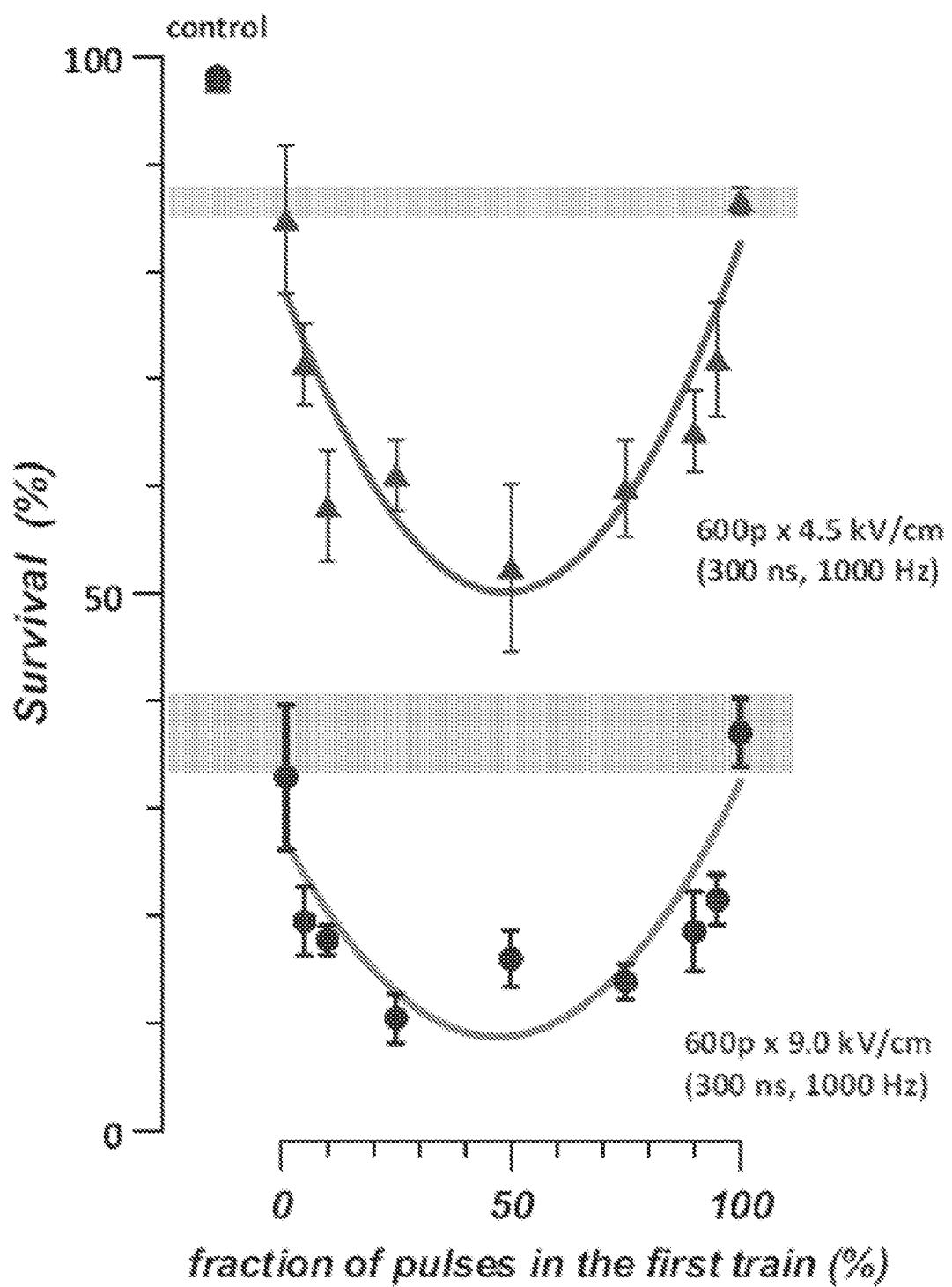
FIG. 3 is an x-y plot showing survival as a function of the fraction of pulses in the first train for a field of 4.5 kV/cm (top) and 9.0 kV/cm (bottom)

Turning now to FIG. 3, there is shown is an x-y plot showing survival as a function of the fraction of pulses in the first train for a field of 4.5 kV/cm (top) and 9.0 kV/cm (bottom). As shown in FIG. 3, the role of fraction size in the enhancement of the EP effect is by fractionation. Survival of U937 cells was determined by propidium exclusion at 4 hr following exposure to 0.3 µs EPs at either 4.5 kV/cm (top graph) or 9 kV/cm. The total number of 600 pulses was split into two fractions which were delivered with a 6-min interval. The number of pulses in the first train varied from 1% to 100% of the total. For example, 1% dose fraction in the 1st train corresponded to 6 pulses in the first train followed by 594 in the 2nd train 6 min later; 10% was 60 pulses in the 1st train and 540 in the 2nd one, and so forth. Although the best fit curves showed maximum efficiency as dose fraction ratio approached 50%, the effect was essentially flat within a wide range of dose fractions, from 10-20 to 80-90%. However, with the smallest fraction (1%), the effect was not different from a single-train exposure, irrespective of the fact that the fractionated exposure lasted 6 min and the single train was delivered in 0.6 s. The 100% value corresponded to delivering all pulses in a single train, and the respective survival levels are shown by shaded areas. Mean+/−s.e., n=4-6. Solid lines are best fit approximations using second degree polynomial function. As shown in FIG. 3, most effective fractions are between 25% and 75%, such as between 40% and 60%. In fact, the solid line for both sets of data is at a minimum at approximately 50%, showing that substantially equal pulse trains would be the most effective.

EP-Induced Propidium Uptake and Membrane Rupture in Substrate-Attached Cells

Several earlier studies attributed the enhanced effect of low PRF to slow, random rotation of cells in suspension, so that different portions of cell membrane face the electrodes and get permeabilized by EP [11, 31]. While this explanation did not explain well the observations described above, the only way to unequivocally rule out the impact of rotation was to replicate the findings in substrate-attached cells. In addition, it was deemed important to replicate the principal findings about PRF and fractionation using a different EP generation and delivery setup, different experiment protocol, and making measurements in individual selected cells rather than in bulk suspension.

A confocal microscope setup for EP exposure of individual cells was used to monitor and quantify propidium (Pr) uptake in CHO cells attached to a coverslip. At high enough treatment intensity (we used a train of 100 pulses, 60 ns duration, at 13.3 kV/cm), the exposure could cause two distinct types of Pr uptake: a transient uptake (during and immediately after EP) and a delayed, accelerated uptake, as shown in FIG. 4.

Figure 4:
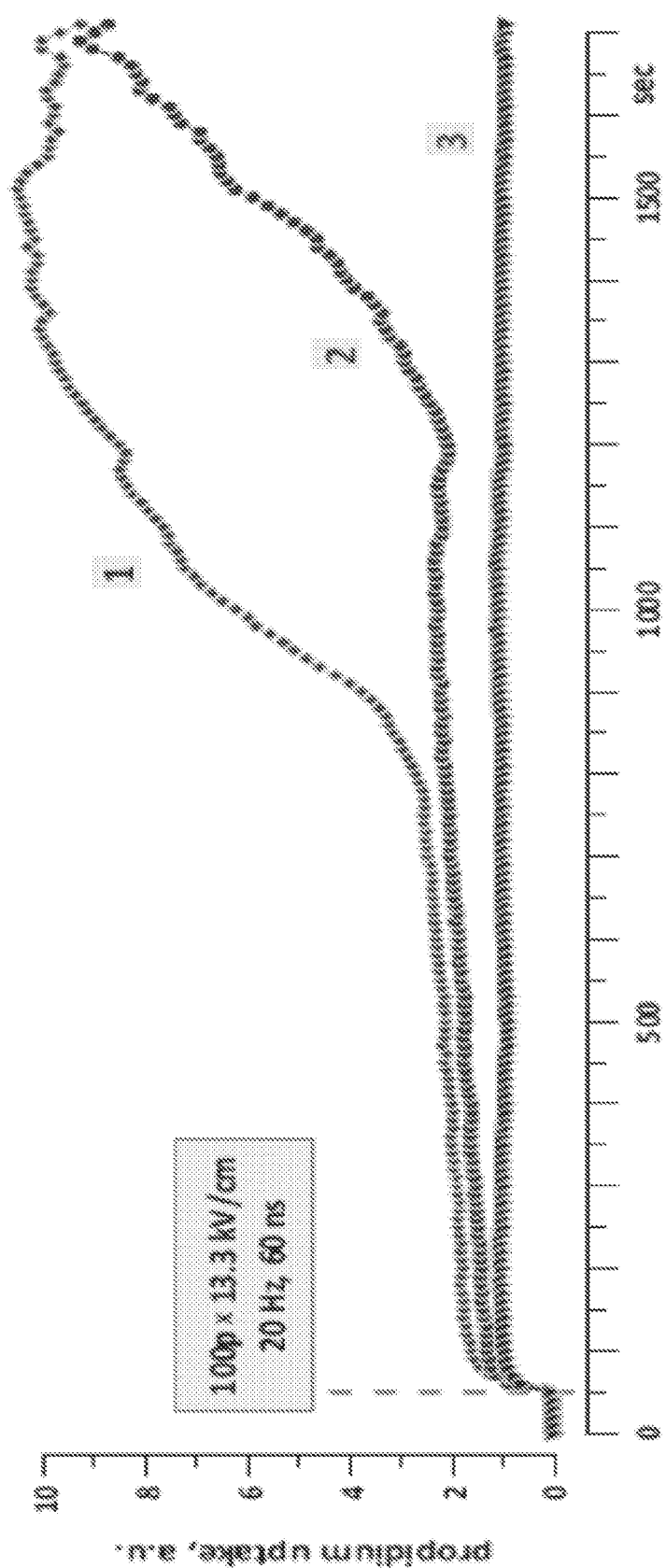
FIG. 4 is an x-y plot showing propidium uptake as a function of time for three CHO cells (1, 2, 3) exposed to an EP train of 100 60 ns pulses with an amplitude of 13.3 kV/cm at a pulse repetition rate of 20 Hz.
Figure 5A:
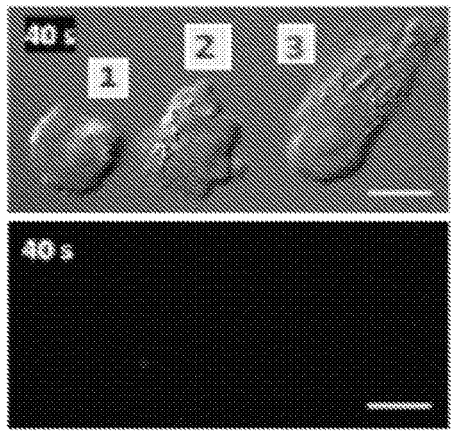
FIGS. 5A-5E show differential-interference contrast and fluorescent images of the cells at selected timepoints.
Figure 5B:
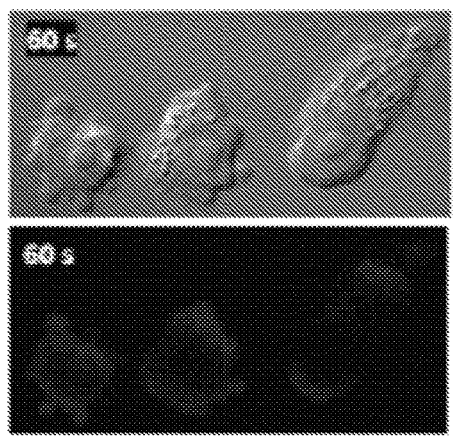
Figure 5C:
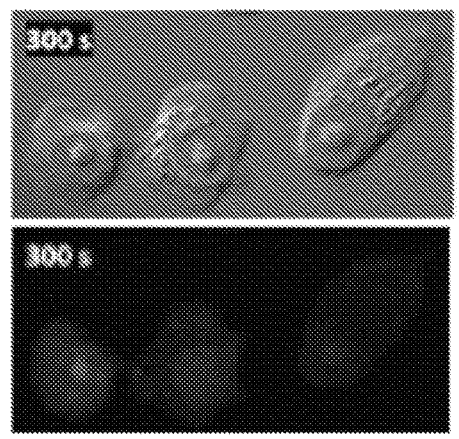
Figure 5D:
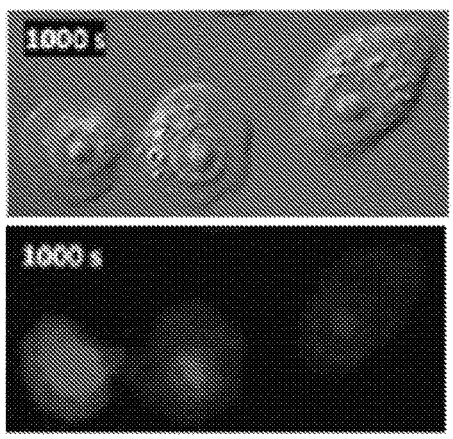
Figure 5E:
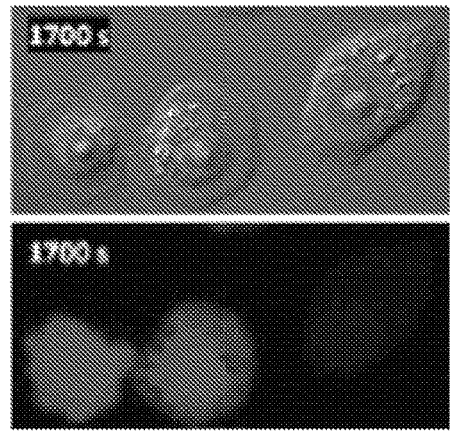

FIG. 4 is an x-y plot showing propidium uptake as a function of time for three CHO cells (1, 2, 3) exposed to an EP train of 100 60 ns pulses with an amplitude of 13.3 kV/cm at a pulse repetition rate of 20 Hz. As shown in FIG. 4, there appear to be two distinct modes of propidium uptake in EP-exposed cells. For FIG. 4, the group of three CHO cells was attached to a coverslip was exposed to the EP train at 50 s into the experiment. FIGS. 5A-5E show differential-interference contrast and fluorescent images of the cells at selected timepoints. The images were taken every 10 s throughout the experiment. The graph shows the time dynamics of Pr uptake by cells 1, 2 and 3. Note the immediate increase in Pr fluorescence in all three cells, caused by electropore opening and transient Pr uptake. Following the transient uptake, the intensity of fluorescence displayed little changes until membrane rupture and massive Pr entry in cells 1 and 2, but not in cell 3.

The transient uptake was characterized by an abrupt increase of the fluorescent signal during and immediately after the exposure, reflecting Pr entry and binding to nucleic acids. Pr fluorescence due to the transient uptake reached a plateau within about 1 min, and remained at this level for the rest of the observation period (30 min).

In some EP-treated cells, the transient uptake was eventually followed by a delayed, more intense, and gradually accelerating Pr uptake (until reaching the detector saturation). Whereas the transient uptake is an immediate and direct manifestation of electroporation, the delayed/accelerated uptake is a sign of irreversible membrane rupture when a cell fails to promptly repair the EP-induced membrane lesions. These two modes of Pr uptake were also reported by other investigators for nano- and microsecond duration EP treatments [45]; the most likely reason for delayed membrane rupture is limited electropore permeability and gradual cell swelling by the colloid osmotic mechanism [46, 47].

Figure 6A:
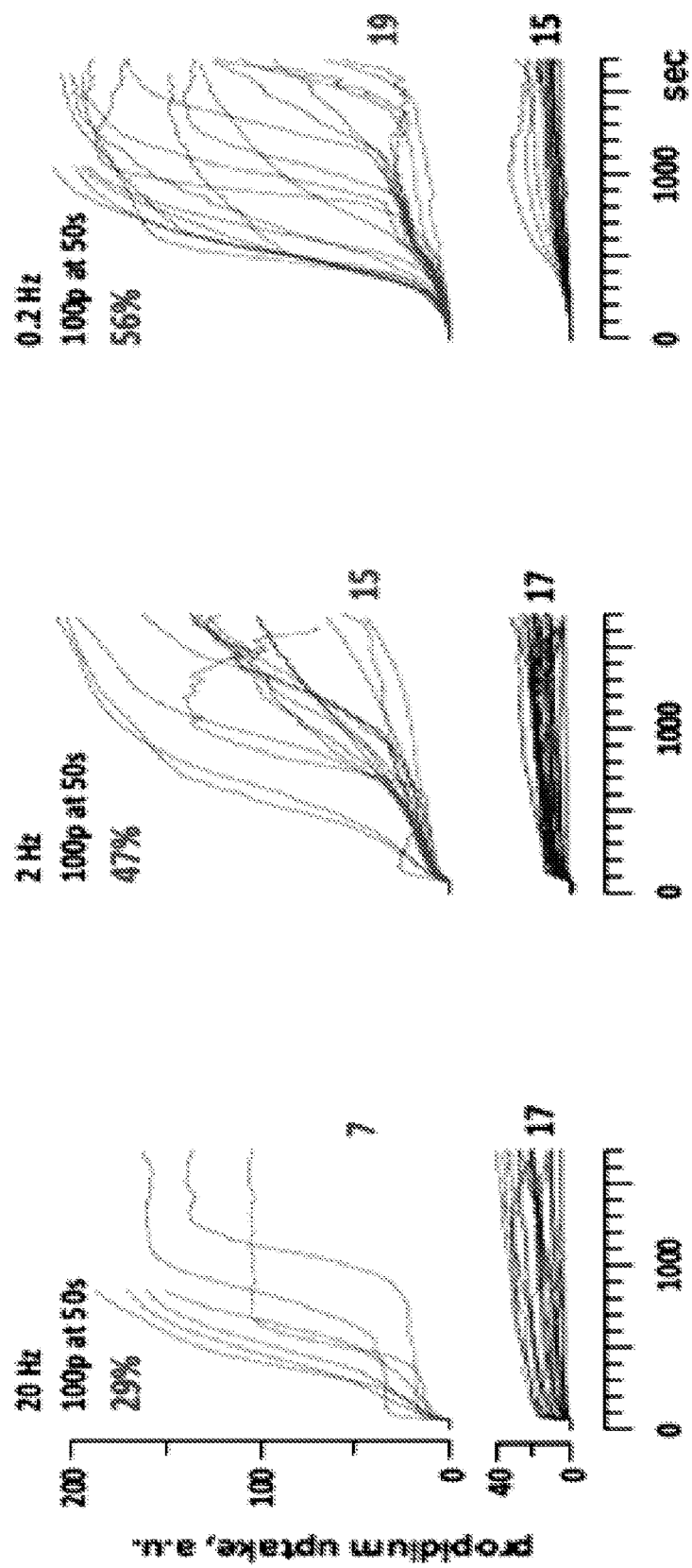
FIGS. 6A and 6B are a series of x-y plots of propidium uptake as a function of time without (FIG. 6A) and with (FIG. 6B) exposure fractionation.
Figure 6B:
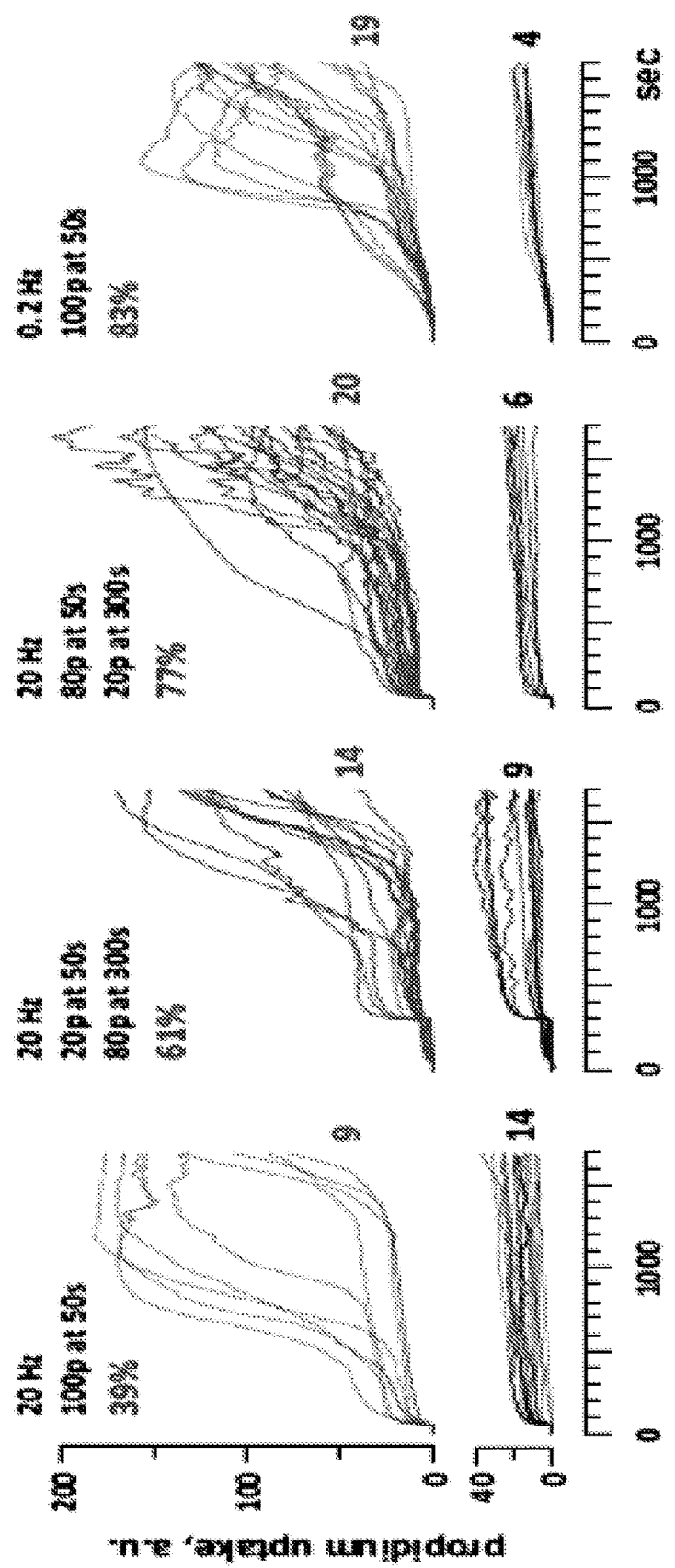

FIGS. 6A and 6B are a series of x-y plots of propidium uptake as a function of time without (FIG. 6A) and with (FIG. 6B) exposure fractionation. These figures show the effect of PRF (FIGS. 6A and 6B) and exposure fractionation (FIG. 6B) on the incidence of delayed membrane rupture in EP-exposed CHO cells.

The experiments for FIGS. 6A and 6B were separate and independent series of experiments. Within each series, different exposure regimens were alternated in random order. Membrane integrity was probed by Pr uptake; each curve corresponds to Pr uptake in an individual exposed cell, as measured by cell imaging every 10 s throughout the experiment. EP exposure caused transient Pr uptake due to electroporation in all cells and delayed/accelerated Pr uptake due to secondary membrane rupture in some cells, as discussed above with respect to FIGS. 4 and 5A-5E. For clarity, for each type of treatment, cells that showed only transient Pr uptake (bottom graphs) were separated from cells that showed both transient and delayed Pr uptake (top graphs). The number of cells that fell into each of the two categories is shown to the right of the graphs. In all groups, cells were exposed to 100, 60 ns pulses at 13.3 kV/cm, whereas the PRF and pulse delivery protocols varied (see legends in the figure). The legends also give the percent of ruptured cells in each group.

FIG. 6A shows that the incidence of membrane rupture resulting from exposure to a single EP train increased with decreasing the PRF, namely from 29% at 20 Hz to 47% at 2 Hz, and 56% at 0.01 Hz. Same as in the cell survival experiments described above, the lowest PRF was the most efficient. FIG. 6B shows a separate set of experiments, where 20 Hz and 0.2 Hz treatments served both as an independent replication of the experiments fog FIG. 6A, and as reference points for efficiency of the fractionated 20 Hz exposures. For unknown reasons, the effects of both 20- and 0.2 Hz exposures in FIG. 6B were somewhat greater than previously shown in FIG. 6A ($p>0.05$), but the higher efficiency of the 0.2 Hz compared to 20 Hz (single train) remained very consistent ($p<0.002$ for FIGS. 6A and 6B data pooled together, two-tailed Fisher Exact Probability test). Both fractionated 20 Hz exposures (20+80 pulses or 80+20 pulses, with 250-s interval) were more effective than a single 20 Hz train, approaching the efficiency of the 0.2 Hz exposure.

Overall, the PRF and dose fractionation had the same effect in the attached cells as in the suspended cells (as described in the previous sections), despite looking at a different endpoints, using shorter (60-ns) EP, and employing an entirely different setup for EP generation and delivery.

Effective Dose Reduction by Fractionation of Exposure

In experiments described above, pulse delivery protocols were changed while keeping the exposure dose constant (including same E-field, same number and duration of pulses). Now, we chose two exposure protocols (a single high-rate train versus same train split in two fractions) and compared their efficiencies within a wide range of doses. These are shown in FIGS. 7A and 7B.

Figure 7A:
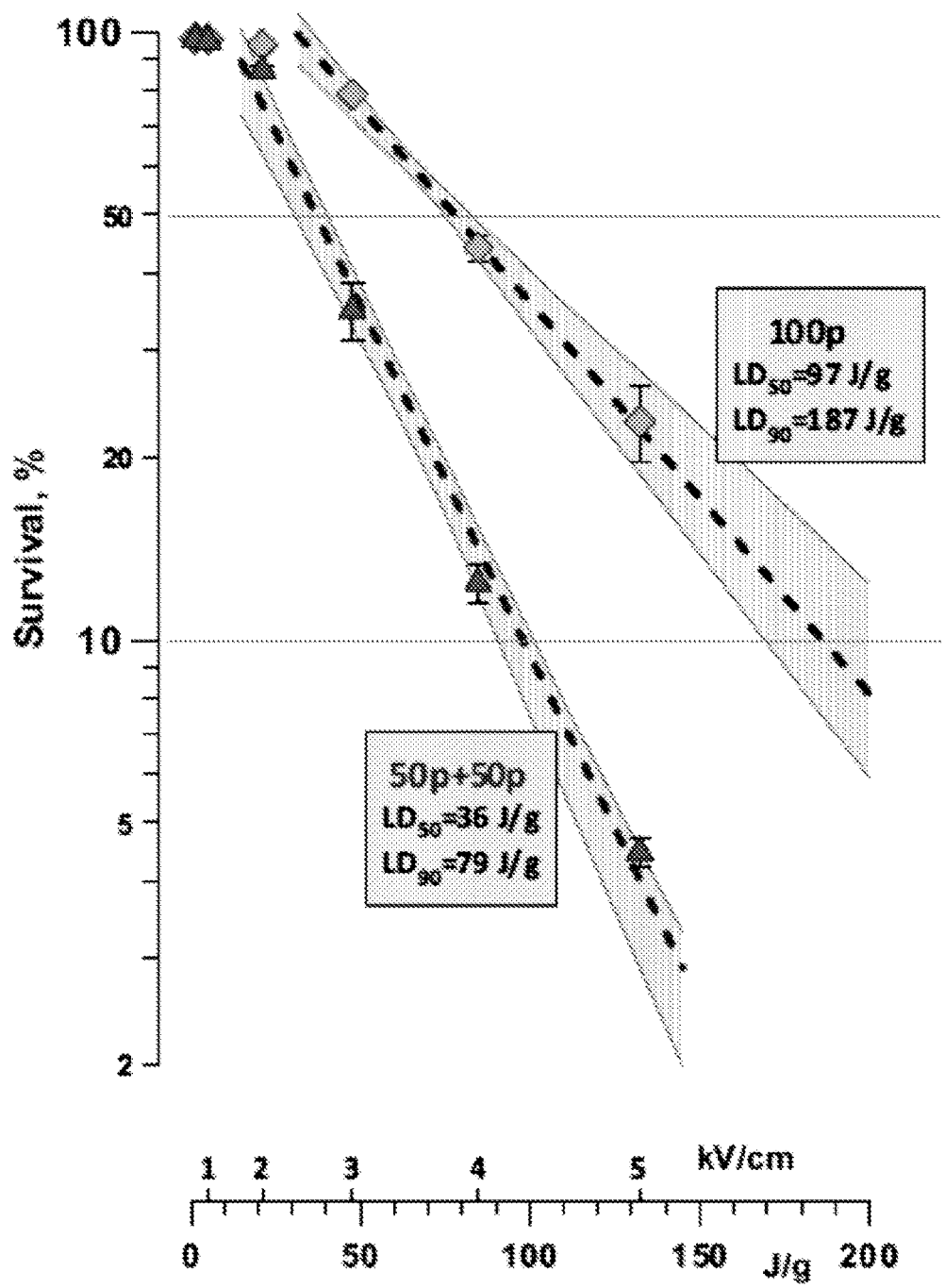
FIGS. 7A and 7B are log-linear plots of survival as a function of absorbed dose U937 cells exposed to 100 and 200, respectively, 0.3 μs duration EPs.
Figure 7B:
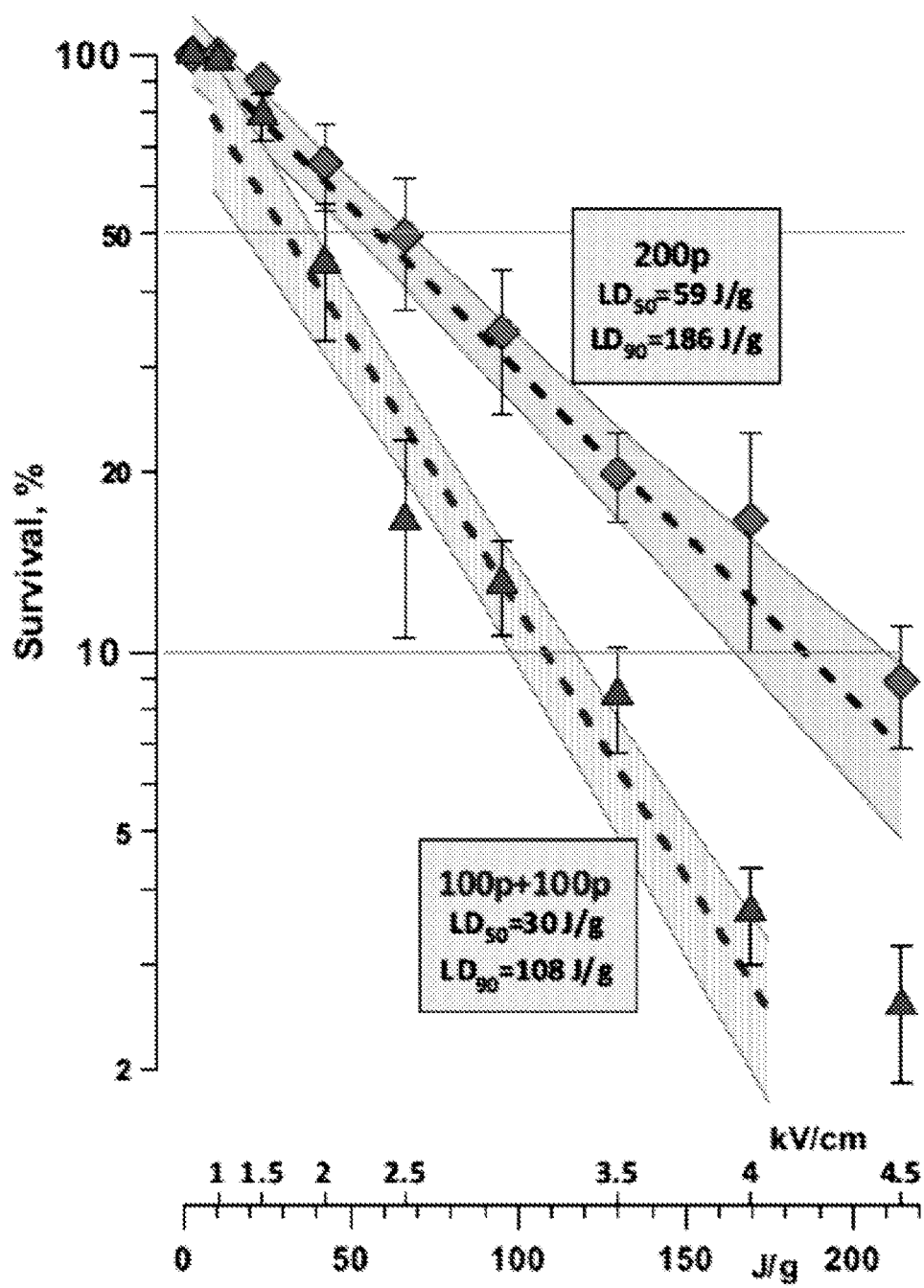

FIGS. 7A and 7B are log-linear plots of survival as a function of absorbed dose U937 cells exposed to 100 and 200, respectively, 0.3 μs duration EPs. The exposure was delivered either as a single train or as two equal fractions (50+50 and 100+100) with a 5-min interval. EPs were applied at different E-fields amplitudes (values are given above the abscissa), resulting in different absorbed doses. The graphs show cell survival (mean+/−s.e., n=3-6) versus the dose for different EP treatments. Dashed lines are the best fit data approximations using exponential function; shaded areas denote 95% confidence intervals. Cell survival was measured by propidium exclusion at 4 hr post exposure. Legends show LD values for elimination of 50% and 90% of cells ($LD_{50}$ and $LD_{90}$) by the tested exposure protocols.

As shown in FIGS. 7A and 7B, the same cytotoxic effect was achieved at significantly lower doses when using the fractionated treatment. Thus an effective reduction of the lethal dose (LD) is provided by exposure fractionation. That is, doses that killed 50% and 90% of cells ($LD_{50}$ and $LD_{90}$) were 2-2.5 times lower for the fractionated exposures. This result can potentially be further improved by adjustment of different exposure parameters.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

REFERENCES

1. Sersa G, Kranjc S, Scancar J, Krzan M, Cemazar M: Electrochemotherapy of Mouse Sarcoma Tumors Using Electric Pulse Trains with Repetition Frequencies of 1 Hz and 5 kHz. *The Journal of Membrane Biology* 2010, 236:155-162.
2. Raeisi E, Firoozabadi S M P, Hajizadeh S, Rajabi H, Hassan Z M: The Effect of High-Frequency Electric Pulses on Tumor Blood Flow In Vivo. *The Journal of Membrane Biology* 2010, 236:163-166.
3. Faurie Cc, Rebersek M, Golzio M, Kanduser M, Escoffre J-M, Pavlin M, Teissie J, Miklavcic D, Rols M-P: Electromediated gene transfer and expression are controlled by the life-time of DNA/membrane complex formation. *The Journal of Gene Medicine* 2010, 12:117-125.
4. Ball C, Thomson K R, Kavnoudias H: Irreversible Electroporation. *Anesthesia & Analgesia* 2010, 110:1305-1309.
5. Maor E, Ivorra A, Rubinsky B: Non thermal irreversible electroporation: novel technology for vascular smooth muscle cells ablation. *PLoS One* 2009, 4:e4757.
6. Rubinsky J, Onik G, Mikus P, Rubinsky B: Optimal Parameters for the Destruction of Prostate Cancer Using Irreversible Electroporation. *The Journal of Urology* 2008, 180:2668-2674.
7. Rubinsky B (Ed.). Irreversible Electroporation. Berlin Heidelberg: Springer-Verlag; 2010.
8. Pakhomov A G, Miklavcic D, Markov M S (Eds.): Advanced Electroporation Techniques in Biology in Medicine. Boca Raton: CRC Press; 2010.

9. Ibey B L, Pakhomov A G, Gregory B W, Khorokhorina V A, Roth C C, Rassokhin M A, Bernhard J A, Wilmink G J, Pakhomova O N: Selective cytotoxicity of intense nanosecond-duration electric pulses in mammalian cells. *Biochim Biophys Acta* 2010, 1800:1210-1219.
10. Ibey B L, Mixon D G, Payne J A, Bowman A, Sickendick K, Wilmink G J, Roach W P, Pakhomov A G: Plasma membrane permeabilization by trains of ultrashort electric pulses. *Bioelectrochemistry* 2010, 79:114-121.
11. Schoenbach K, Joshi R, Beebe S, Baum C: A scaling law for membrane permeabilization with nanopulses. *IEEE Transactions on Dielectrics and Electrical Insulation* 2009 16:1224-1235.
12. Pakhomov A G, Bowman A M, Ibey B L, Andre F M, Pakhomova O N, Schoenbach K H: Lipid nanopores can form a stable, ion channel-like conduction pathway in cell membrane. *Biochem Biophys Res Commun* 2009, 385: 181-186.
13. Nuccitelli R, Chen X, Pakhomov A G, Baldwin W H, Sheikh S, Pomicter J L, Ren W, Osgood C, Swanson R J, Kolb J F, et al: A new pulsed electric field therapy for melanoma disrupts the tumor's blood supply and causes complete remission without recurrence. *Int J Cancer* 2009, 125:438-445.
14. Nuccitelli R, Tran K, Sheikh S, Athos B, Kreis M, Nuccitelli P: Optimized nanosecond pulsed electric field therapy can cause murine malignant melanomas to self-destruct with a single treatment. *International Journal of Cancer* 2010, 127:1727-1736.
15. Heller L C, Heller R: Electroporation gene therapy preclinical and clinical trials for melanoma. *Curr Gene Ther* 2010, 10:312-317.
16. Esser A T, Smith K C, Gowrishankar T R, Vasilkoski Z, Weaver J C: Mechanisms for the Intracellular Manipulation of Organelles by Conventional Electroporation. *Biophysical Journal* 2010, 98:2506-2514.
17. Andre F M, Gehl J, Sersa G, Preat V, Hojman P, Eriksen J, Golzio M, Cemazar M, Payselj N, Rols M P, et al: Efficiency of high- and low-voltage pulse combinations for gene electrotransfer in muscle, liver, tumor, and skin. *Hum Gene Ther* 2008, 19:1261-1271.
18. Escoffre J M, Portet T, Wasungu L, Teissie J, Dean D, Rols M P: What is (still not) known of the mechanism by which electroporation mediates gene transfer and expression in cells and tissues. *Mol Biotechnol* 2009, 41:286-295.
19. Faurie C, Rebersek M, Golzio M, Kanduser M, Escoffre J M, Pavlin M, Teissie J, Miklavcic D, Rols MP: Electro-mediated gene transfer and expression are controlled by the life-time of DNA/membrane complex formation. *J Gene Med* 2010, 12:117-125.
20. Mir L M: Nucleic acids electrotransfer-based gene therapy (electrogenetherapy): past, current, and future. *Mol Biotechnol* 2009, 43:167-176.
21. Tiwari J K, Poonam, Sarkar D, Pandey S K, Gopal J, Kumar S R: Molecular and morphological characterization of somatic hybrids between *Solanum tuberosum* L. and *S. etuberosum* Lindl. Plant Cell Tiss Org 2010, 103:175-187.
22. Terpitz U, Raimunda D, Westhoff M, Sukhorukov V L, Beauge L, Bamberg E, Zimmermann D: Electrofused giant protoplasts of *Saccharomyces cerevisiae* as a novel system for electrophysiological studies on membrane proteins. *Biochim Biophys Acta* 2008, 1778:1493-1500.
23. Neumann E, Sowers A E, Jordan C A (Eds.): Electroporation and Electrofusion in Cell Biology. New York: Plenum; 1989.
24. Sersa G, Miklavcic D, Cemazar M, Rudolf Z, Pucihar G, Snoj M: Electrochemotherapy in treatment of tumours. *Eur J Surg Oncol* 2008, 34:232-240.
25. Mir L M, Glass L F, Sersa G, Teissie J, Domenge C, Miklavcic D, Jaroszeski M J, Orlowski S, Reintgen D S, Rudolf Z, et al: Effective treatment of cutaneous and subcutaneous malignant tumours by electrochemotherapy. *Br J Cancer* 1998, 77:2336-2342.
26. Al-Sakere B, Andre F, Bernat C, Connault E, Opolon P, Davalos R V, Rubinsky B, Mir L M: Tumor ablation with irreversible electroporation. *PLoS One* 2007, 2:e1135.
27. El-Hag A H, Jayaram S H, Griffiths M W: Inactivation of naturally grown microorganisms in orange juice using pulsed electric fields. *Ieee Transactions on Plasma Science* 2006, 34:1412-1415.
28. Jayaram S H, Boggs S A: Optimization of electroporation waveforms for cell sterilization. *Ieee T Ind Appl* 2004, 40:1489-1497.
29. Sack M, Sigler J, Eing C, Stukenbrock L, Stangle R, Wolf A, Muller G: Operation of an Electroporation Device for Grape Mash. *Ieee Transactions on Plasma Science* 2010, 38:1928-1934.
30. Lebovka N, Vorobiev E: Food and biomaterials processing assisted by electroporation. In *Advanced electroporation techniques in biology and medicine*. Edited by Pakhomov A G, Miklavcic D, Markov M. Boca Raton: CRC Press; 2010: 463-490.
31. Vernhes M-C, Cabanes P-A, Teissie J: Chinese hamster ovary cells sensitivity to localized electrical stresses. *Bioelectrochemistry and Bioenergetics* 1999, 48:17-25.
32. Schoenbach K S, Hargrave B, Joshi R P, Kolb J, Osgood C, Nuccitelli R, Pakhomov A G, Swanson J, Stacey M, White J A, et al: Bioelectric Effects of Nanosecond Pulses. *IEEE Transactions on Dielectrics and Electrical Insulation* 2007, 14:1088-1109.
33. Teissie J, Eynard N, Vernhes M C, Benichou A, Ganeva V, Galutzov B, Cabanes P A: Recent biotechnological developments of electropulsation. A prospective review. *Bioelectrochemistry* 2002, 55:107-112.
34. Lebar A M, Troiano G C, Tung L, Miklavcic D: Inter-pulse interval between rectangular voltage pulses affects electroporation threshold of artificial lipid bilayers. *IEEE Trans Nanobioscience* 2002, 1:116-120.
35. Vernier P T, Sun Y, Gundersen M A: Nanoelectropulse-driven membrane perturbation and small molecule permeabilization. *BMC Cell Biol* 2006, 7:37.
36. Jiang N, Cooper B Y: Frequency-dependent interaction of ultrashort E-fields with nociceptor membranes and proteins. *Bioelectromagnetics* 2010:n/a-n/a.
37. Matsuki N, Ishikawa T, Imai Y, Yamaguchi T: Low voltage pulses can induce apoptosis. *Cancer Lett* 2008, 269:93-100.
38. Yang X-J, Li J, Sun C—X, Zheng F-Y, Hu L-N: The effect of high frequency steep pulsed electric fields on in vitro and in vivo antitumor efficiency of ovarian cancer cell line skov3 and potential use in electrochemotherapy. *Journal of Experimental & Clinical Cancer Research* 2009, 28:53.
39. Miller L, Leor J, Rubinsky B: Cancer cells ablation with irreversible electroporation. *Technol Cancer Res Treat* 2005, 4:699-705.
40. Pucihar G, Mir L M, Miklavcic D: The effect of pulse repetition frequency on the uptake into electropermeabilized cells in vitro with possible applications in electrochemotherapy. *Bioelectrochemistry* 2002, 57:167-172.
41. Bilska A O, DeBruin K A, Krassowska W: Theoretical modeling of the effects of shock duration, frequency, and strength on the degree of electroporation. *Bioelectrochemistry* 2000, 51:133-143.
42. Marty M, Sersa G, Garbay J R, Gehl J, Collins C G, Snoj M, Billard V, Geertsen P F, Larkin J O, Miklavcic D, et al: Electrochemotherapy—An easy, highly effective and safe treatment of cutaneous and subcutaneous metastases: Results of ESOPE (European Standard Operating Procedures of Electrochemotherapy) study. *Ejc Suppl* 2006, 4:3-13.
43. Zupanic A, Ribaric S, Miklavcic D: Increasing the repetition frequency of electric pulse delivery reduces unpleasant sensations that occur in electrochemotherapy. *Neoplasma* 2007, 54:246-250.
44. Miklavcic D, Pucihar G, Pavlovec M, Ribaric S, Mali M, Macek-Lebar A, Petkovsek M, Nastran J, Kranjc S, Cemazar M, Sersa G: The effect of high frequency electric pulses on muscle contractions and antitumor efficiency in vivo for a potential use in clinical electrochemotherapy. *Bioelectrochemistry* 2005, 65:121-128.
45. Kennedy S M, Ji Z, Hedstrom J C, Booske J H, Hagness S C: Quantification of electroporative uptake kinetics and electric field heterogeneity effects in cells. *Biophys J* 2008, 94:5018-5027.
46. Tsong T Y: Electroporation of cell membranes. *Biophys J* 1991, 60:297-306.
47. Pakhomov A G, Pakhomova O N: Nanopores: A distinct transmembrane passageway in electroporated cells. In *Advanced Electroporation Techniques in Biology in Medicine*. Edited by Pakhomov A G, Miklavcic D, Markov M S. Boca Raton: CRC Press; 2010: 178-194
48. Idone V, Tam C, Andrews N W: Two-way traffic on the road to plasma membrane repair. *Trends Cell Biol* 2008, 18:552-559.
49. Idone V, Tam C, Goss J W, Toomre D, Pypaert M, Andrews N W: Repair of injured plasma membrane by rapid Ca2+-dependent endocytosis. *J Cell Biol* 2008, 180:905-914.
50. Kinosita K, Jr., Tsong T Y: Formation and resealing of pores of controlled sizes in human erythrocyte membrane. *Nature* 1977, 268:438-441.
51. Pakhomov A G, Phinney A, Ashmore J, Walker K, J. K, Kono S, Schoenbach K S, Murphy M R: Characterization of the cytotoxic effect of high-intensity, 10-ns duration electrical pulses. *IEEE Transactions on Plasma Science* 2004, 32:1579-1585.
52. Walker K, 3rd, Pakhomova O N, Kolb J, Schoenbach K S, Stuck B E, Murphy M R, Pakhomov A G: Oxygen enhances lethal effect of high-intensity, ultrashort electrical pulses. *Bioelectromagnetics* 2006, 27:221-225.
53. Bonnafous P, Vernhes M, Teissie J, Gabriel B: The generation of reactive-oxygen species associated with long-lasting pulse-induced electropermeabilisation of mammalian cells is based on a non-destructive alteration of the plasma membrane. *Biochim Biophys Acta* 1999, 1461:123-134.
54. Vernier P T, Levine Z A, Wu Y H, Joubert V, Ziegler M J, Mir L M, Tieleman D P: Electroporating fields target oxidatively damaged areas in the cell membrane. *PLoS One* 2009, 4:e7966.
55. Bowman A M, Nesin O M, Pakhomova O N, Pakhomov A G: Analysis of Plasma Membrane Integrity by Fluorescent Detection of Tl(+) Uptake. *J Membr Biol* 2010.

What is claimed is:

1. A method of enhancing membrane permeabilization in at least one cell, comprising:
    (a) disposing the at least one cell between a first electrode and a second electrode; and
    (b) applying an electric pulse (EP) treatment using the first electrode and the second electrode,
    wherein the EP treatment comprises a plurality of electrical pulses between the first electrode and the second electrode, wherein the plurality of electrical pulses consists of a first train of pulses and a second train of pulses separated by an interval, wherein the interval is at least 10 s, and wherein an amplitude of the plurality of electrical pulses is greater than about 0.2 kV/cm,
    wherein the plurality of electrical pulses comprises at least 100 pulses, wherein a duration of time for the plurality of electrical pulses EP treatment is greater than about 10 s and less than or equal to 1000 s, and
    wherein a range of the duration of the plurality of electrical pulses is substantially the same for each of the first train of pulses and the second train of pulses.

2. The method of claim 1, wherein the amplitude is between about 0.2 kV/cm and 15 kV/cm.

3. The method claim 1, wherein the plurality of electrical pulses comprises less than about 1500 pulses.

4. The method of claim 1, wherein the number of electrical pulses in the first train and the second train are substantially the same.

5. The method of claim 1, wherein the first train and the second train are different.

6. The method of claim 1, wherein a number of electrical pulses in the first train comprises 25% to 75% of the plurality of electrical pulses.

7. The method of claim 1, wherein the at least one cell is one of a cancerous cell, a mammalian cell, a bacterial cell, or a plant cell.

8. The method of claim 1, further comprising introducing a therapeutic agent into the at least one cell, wherein the therapeutic agent is selected from the group consisting of: nucleic acid, peptide, polypeptide, and drug.

9. The method of claim 1, wherein enhancing membrane permeabilization in the at least one cell results in rupturing of the membrane and in death of the at least one cell.

10. The method of claim 1, wherein disposing the at least one cell between the first electrode and the second electrode comprises disposing a volume of liquid including the at least one cell between the first electrode and the second electrode.

11. The method of claim 1, wherein a range of the amplitude of the plurality of electrical pulses is substantially the same for each of the first train of pulses and the second train of pulses.

12. The method of claim 1, wherein the interval is between about 150 s and 300 s and the duration of time for the EP treatment is greater than about 150 s and less than or equal to 1000 s.

13. The method of claim 1, wherein the plurality of pulses comprises individual pulses with duration of about 300 ns to 9 µs.

14. A method of introducing a therapeutic agent into at least one cell, comprising:
    disposing the at least one cell between a first electrode and a second electrode;
    applying an electric pulse (EP) treatment using the first electrode and the second electrode; and
    prior to or subsequent to the EP treatment, supplying the therapeutic agent to the at least one cell;
    wherein the EP treatment comprises a plurality of electrical pulses between the first electrode and the second electrode,
    wherein the plurality of electrical pulses consists of a first train of pulses and a second train of pulses separated by an interval, wherein the interval is at least 10 s, wherein an amplitude of the plurality of electrical pulses is greater than about 0.2 kV/cm, wherein the plurality of electrical pulses comprises at least 100 pulses, wherein a duration of time for the plurality of electrical pulses EP treatment is between greater than about 10 s and less than or equal to 1000 s, and wherein a range of the duration of the plurality of electrical pulses is substantially the same for each of the first train of pulses and the second train of pulses.

15. The method of claim 14, wherein the amplitude is between about 0.2 kV/cm and 15 kV/cm.

16. The method of claim 14, wherein the plurality of electrical pulses comprises less than about 1500 pulses.

17. The method of claim 14, wherein the first train and the second train are substantially the same.

18. The method of claim 14, wherein the first train and the second train are different.

19. The method of claim 14, wherein a number of electrical pulses in the first train is different than a number of electrical pulses in the second train such that the first train comprises 25% to 75% of the plurality of electrical pulses.

20. The method of claim 14, wherein the at least one cell is a mammalian cell.

21. The method of claim 14, wherein the therapeutic agent is selected from the group consisting of: nucleic acid, peptide, polypeptide, and drug.

* * * * *